(12) United States Patent
Lee et al.

(10) Patent No.: US 11,123,361 B2
(45) Date of Patent: *Sep. 21, 2021

(54) DOUBLE-STRANDED OLIGO RNA STRUCTURE COMPRISING MIRNA

(71) Applicant: BIONEER CORPORATION, Daejeon (KR)

(72) Inventors: Taewoo Lee, Seoul (KR); Sanghyung Shim, Daejeon (KR); Ungsik Yu, Daejeon (KR); Han-Oh Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/302,670

(22) PCT Filed: Aug. 24, 2017

(86) PCT No.: PCT/KR2017/009271
§ 371 (c)(1),
(2) Date: Nov. 18, 2018

(87) PCT Pub. No.: WO2018/038558
PCT Pub. Date: Mar. 1, 2018

(65) Prior Publication Data
US 2020/0179432 A1    Jun. 11, 2020

(30) Foreign Application Priority Data
Aug. 24, 2016    (KR) .................. 10-2016-0107937

(51) Int. Cl.
*A61K 48/00*    (2006.01)
*C12N 15/11*    (2006.01)
(Continued)

(52) U.S. Cl.
CPC ............ *A61K 31/713* (2013.01); *A61K 31/25* (2013.01); *A61P 35/00* (2018.01); *C12N 15/1135* (2013.01); *C12N 2310/141* (2013.01)

(58) Field of Classification Search
CPC .............. C12N 15/113; C12N 15/1135; C12N 2310/141; C12N 2310/351; A61K 31/713; A61K 47/60
See application file for complete search history.

(56) References Cited

U.S. PATENT DOCUMENTS 9,326,941 B2 *    5/2016    Chae .................. A61K 9/14
10,030,243 B2 *    7/2018    Park .................. A61P 43/00
(Continued)

FOREIGN PATENT DOCUMENTS

EP    3108209 A2    5/2016
EP    3128008 A2    2/2017
(Continued)

OTHER PUBLICATIONS

Cancer Research Wales. No Two Cancers are the Same, https://www.cancerresearchwales.co.uk/blog/no-two-cancers-are-the-same, downloaded on Aug. 19, 2020.*
(Continued)

*Primary Examiner* — Terra C Gibbs
(74) *Attorney, Agent, or Firm* — Hultquist, PLLC; Steven J. Hultquist (57) ABSTRACT

The present invention relates to a double-stranded oligo RNA structure comprising double-stranded miRNA, and a composition for preventing or treating cancer, containing the same. More specifically, the present invention relates to an anti-cancer pharmaceutical composition, containing: a double-stranded oligo RNA structure comprising miR-3670, miR-4477a and miR-8078, and characterized by a method for effectively inhibiting cancer cell proliferation or induc-
(Continued)

ing cancer cell apoptosis; and a pharmaceutically acceptable carrier.

15 Claims, 4 Drawing Sheets
(3 of 4 Drawing Sheet(s) Filed in Color)
Specification includes a Sequence Listing.

(51) Int. Cl.

| C07H 21/02 | (2006.01) |
|---|---|
| C07H 21/04 | (2006.01) |
| A61K 31/713 | (2006.01) |
| A61P 35/00 | (2006.01) |
| A61K 31/25 | (2006.01) |
| C12N 15/113 | (2010.01) |

(56) References Cited

U.S. PATENT DOCUMENTS 10,351,849 B2 * 7/2019 Lee .................. A61P 35/00
2009/0227533 A1 9/2009 Bader et al.

FOREIGN PATENT DOCUMENTS

| KR | 10-0883471 B1 | 2/2009 |
|---|---|---|
| KR | 1020090081125 A | 7/2009 |
| KR | 101224828 B | 1/2013 |
| KR | 101224828 B1 | 1/2013 |
| KR | 1020160033125 B | 3/2016 |
| WO | 2014100252 A1 | 6/2014 |
| WO | 2015005670 A1 | 1/2015 |
| WO | 2015152693 A2 | 10/2015 |
| WO | 2016137235 A2 | 9/2016 |

OTHER PUBLICATIONS

Will Glower. No, you cannot prevent all cancers, https://time.com/4519760/no-you-cant-prevent-all-cancers/ downloaded on Aug. 19, 2020.*
American Cancer Society Pancreatic Cancer Causes, Risk Factors, and Prevention, https://www.cancer.org/cancer/pancreatic-cancer/causes-risks-prevention/risk-factors.html downloaded on Aug. 19, 2020.*
Cleveland Clinic. Liver Cancer: Prevention, https://my.clevelandclinic.org/health/diseases/9418-liver-cancer/prevention downloaded on Aug. 19, 2020.*
Montanucci et al. (The Open Applied Informatics Journal 2(1) Jun. 2007, pp. 1-8).*
Zeng et al. (PNAS, 2003 vol. 100:9779-9784).*
Doench et al. (Genes & Development, 2003 vol. 17:438-442).*
Lam et al. (MolecularTherapy, 2015 vol. 4:pp. 1-19).*
Bajan et al. (Cells, 2020 vol. 9:pp. 1-27).*
Agostini, M., et al., "miR-34: from bench to bedside", "Oncotarget", Mar. 15, 2014, pp. 872-881, vol. 5, No. 4, Publisher: www.impactjournals.com/oncotarget.
Bartel, D., "MicroRNA Target Recognition and Regulatory Functions", "Cell", Jan. 23, 2009, pp. 215-233, vol. 136, No. 2, Publisher: NIH Public Access.
Bartolome, R., et al., "IL13 Receptor a2 Signaling Requires a Scaffold Protein, FAM120A, to Activate the FAK end PI3K Pathways in Colon Cancer Metastasis", "Cancer Research", Jun. 15, 2015, pp. 2434-2444, vol. 75, No. 12, Publisher: American Association for Cancer Research.
Brodersen, P., et al., "Revisiting principles of microRNA target recognition and mode of action", "Nature Reviews/Molecular Cell Biology", Feb. 2009, pp. 141-148, vol. 10, Publisher: Macmillan Publishers Limited.

Burnett, J., et al., "RNA-based Therapeutics—Current Progress and Future Prospects", "Chem Biol.", Jan. 27, 2012, pp. 60-71, vol. 19, No. 1, Publisher: NIH Public Access.
Carthew, R., et al., "Origins and Mechanisims of miRNAs and siRNAs", "Cell", Feb. 20, 2009, pp. 642-655, vol. 136, No. 4, Publisher NIH Public Access.
Chang, T.C., et al., "Transactivation of miR-34a by p53 broadly influences gene expression and promotes apoptosis", "Mol Cell", Jun. 8, 2007, pp. 745-752, vol. 26, No. 5, Publisher NIH Public Access.
Chu, C.Y., et al., "Potent RNAi by short RNA triggers", "RNA", 2008, pp. 1-6, vol. 14, Publisher: Ccole Spring Harbor Laboratory Press.
Dangwal, S., et al., "microRNA Therapeutics in Cardiovascular Disease Models", "The Annual Review of Pharmacology and Toxicology", 2014, pp. 185-203, vol. 54, Publisher: www.annualreviews.org.
Erez, A., et al., "Sil overexpression in lung cancer characterizes tumors with increased mitotic activity", "Oncogene", 2004, pp. 5371-5377, vol. 23, Publisher: Nature Publishing Group.
Erez, A., et al., "The Sil Gene Is Essential for Mitotic Entry and Survival of Cancer Cells", "Cancer Res.", Apr. 24, 2007, pp. 4022-4027 and p. 5998 correction on Jun. 15, 2007, vol. 67, No. 9, Publisher: American Association for Cancer Research.
Fujii, M., et al., "SNIP1 Is a Candidate Modifier of the Transcriptional Activity of c-Myc on E Box-Dependent Target Genes", "Molecular Cell", Dec. 8, 2006, pp. 771-783, vol. 24, Publisher: Elsevier Inc.
"*Homo sapiens* BAC clone CH17-292P3 from chromosome 16, complete sequence, AC269968.1", "GenBank", Sep. 18, 2017, Publisher: NCBI.
Hermeking, H., "The miR-34 family in cancer and apoptosis", "Cell Death and Differentiation", 2010, pp. 193-199, vol. 17, Publisher: Macmillan Publishers Limited.
Huang, X., et al., "RIPK4 phosphorylates Dishevelled proteins to regulate canonical Wnt signaling", "Science", Mar. 22, 2013, pp. 1441-1445, vol. 339, No. 6126, Publisher: NIH Public Access.
Jorns, E., et al., "Utilizing RNA interference to enhance cancer drug discovery", "Nature Reviews/Drug Discovery", Jul. 2007, pp. 556-568, vol. 6, Publisher: Nature Publishing Group.
Jackson, A., et al., "Expression profiling reveals "off-target" gene regulation by RNAi", "Nature Biotechnology", May 2003, pp. 635-637, vol. 21, Publisher: Nature Publishing Group.
Jackson, A., et al., "Position-specific chemical modification of siRNAs reduces "off-target" transcript silencing", "RNA", 2006, vol. 12, No. 1197-1205, Publisher: Cold Spring Harbor Laboratory Press.
Jackson, A., et al., "Widespread siRNA off target transcript silencing mediated by seed region complementarity", "RNA", 2006, pp. 1179-1187, vol. 12, Publisher: Cold Spring Harbor Laboratory Press.
Jeon, H.S., et al., "High expression of SNIP1 correlates with poor prognosis in Non small cell lung cancer and SNIP1 interferes with the recruitment of HDAC1 to RB in vitro", "Lung Cancer", 2013, pp. 24-30, vol. 82, Publisher: Elsevier Ireland Ltd.
Jiao, H-K, et al., "Prognostic significance of Cbx4 expression and its beneficial effect for transarterial mchemoembolization in hepatocellular carcinoma", "Cell Death and Disease", Mar. 12, 2015, p. e1689, vol. 6, Publisher: Macmillan Publishers Limited.
Kim, S., et al., "Local and systemic delivery of VEGF siRNA using polyelectrolyte complex micelles for effective treatment of cander", "Journal of Controlled Release", 2008, pp. 107-116, vol. 129, Publisher: Elsevier.
Landi, D., et al., "Role of variations within microRNA-binding sites in cancer", "Mutagenesis", 2012, pp. 205-210, vol. 27, No. 2, Publisher: Oxford University Press.
Laviolette, L., et al., "17-Estradiol upregulates GREB1 and accelerates ovarian tumor progression in vivo", "International Journal of Cancer", 2014, pp. 1072-1084, vol. 135, Publisher: Wiley Periodicals, Inc.
Li, Q., et al., "SNIP1: a new activator of HSE signaling pathway", "Mol Cell Biochem", 2012, pp. 16, vol. 362, Publisher: Springer Science & Business Media B.V.

(56) References Cited

OTHER PUBLICATIONS

Li, Y., et al., "The HECTD3 E3 ubiquitin ligase facilities cancer cell survival by promoting K63-linked polyubiquitination of caspase-8", "Cell Death and Disease", 2013, pp. 1-11, vol. 4, No. e935, Publisher: Macmillan Publishers Limited.
Li, Y., et al., "The HECTD3 E3 Ubiqitin Ligase Suppressses Cisplatin-Induced Apoptosis via Stabilizing MALT1", "Neoplasia", Jan. 2013, pp. 39-48, vol. 15, No. 1, Publisher: www.neoplasia.com.
Liang, X., et al., "Hypoxia-inducible factor-1 alpha, in association with TWIST2 and SNIP1, is a critical prognostic factor in patients with tongue squamous cell carcinoma", "Oral Oncology", 2011, pp. 92-97, vol. 47, Publisher: Elsevier.
Lin, Z, et al., "MicroRNA-224 inhibits progression of human prostate cancer by downregulating TRIB1", "International Journal fo Cancer", 2014, pp. 541-550, vol. 135, Publisher: UICC.
Logue J., et al., "AKAP220 Protein Organizes Signaling Elements That Impact Cell Migration", "The Journal of Biological Chemistry", Nov. 11, 2011, pp. 39269-39281, vol. 286, No. 45, Publisher: ASBMB.
Malone, C., et al., "Small RNAs as Guardians of the Genome", "Cell", Feb. 20, 2009, pp. 656-668, vol. 136, No. 4, Publisher: NIH Public Access.
Martens-De Kemp, S., et al., "Functional Genetic Screens Identify Genes Essential for Tumor Cell Survival in Head and Neck and Lung Cancer", "Clinical Cancer Research", Apr. 15, 2013, pp. 1994-2003, vol. 19, No. 8, Publisher: American Association for Cancer Research.
Mashidori, T., et al., "Increased alpha-taxilin protein expression is associated with the metastatic and invasive potential of renal cell cancer", "Biomedical Research", 2011, pp. 103-110, vol. 32, No. 2.
Madfarlane, L.-A., et al., "MicroRNA: Biogenesis, Function and Role in Cancer", "Current Genomics", 2010, pp. 537-561, vol. 11, Publisher: Bentham Science Publishers, Ltd.
Mittal, V., "Improving the Efficiency of RNA Interference in Mammals", "Nature Reviews/Genetics", May 2004, pp. 355-365, vol. 5, Publisher: Nature Publishing Group.
Nicoloso, M., et al., "MicroRNAs—the micro steering wheel of tumour metastases", "Nature Reviews/Cancer", Apr. 2009, pp. 293-302, vol. 9, Publisher: Macmillan Publishers Limited.
Nielsen, C., et al., "Detrminants of targeting by endogenous and exogenous microRNAs and siRNAs", "RNA", 2007, pp. 1894-1910, vol. 13, Publisher: Cold Spring Harbor Laboratory Press.
Ohashi, K., et al., "Characteristics of Lung Cancers Harboring NRAS Mutations", "Clin Cancer Res", May 1, 2013, pp. 2584-2591, vol. 19, No. 9, Publisher: NIH Public Access.
Ohtomo, N., et al., "Expression of—taxilin in hepatocellular carcinoma correlates with growth activity and malignant potential of the tumor", "International Journal of Oncology", 2010, pp. 1417-1423, vol. 37.
Orouji, E., et al., "MAP kinase pathway gene copy alterations in NRAS/BRAF wild-type advanced melanoma", "International Journal of Cancer", 2016, pp. 2257-2262, vol. 138, Publisher: UICC.
Pecina-Slaus, N., et al., "Wnt signaling transcription factors TCF-1 and LEF-1 are upregulated in malignant astrocytic brain tumors", "Histology and Histopathology", 2014, pp. 1557-1564, vol. 29, No. 12, Publisher: http://medlib.mef.hr/.
Peek, A., et al., "Design of active small interfering RNAs", "Current Opinion in Molecular Therapeutics", 2007, pp. 110-118, vol. 9, No. 2, Publisher: The Thomson Corporation ISSN.
Rae, J., et al., "GREB1 is a Novel Androgen-Regulated Gene Required for Prostate Cancer Growth", "The Prostate", 2006, pp. 886-894, vol. 66, Publisher: Wiley-Liss, Inc.
Reynolds, A., et al., "Rational siRNA design for RNA interference", "Nature Biotechnology", Mar. 2004, pp. 326-330, vol. 22, No. 3, Publisher: Nature Publishing Group.

"Regulation of ATR-dependent pathways by the FHA domain containing protein SNIP1", "Oncogene", 2007, pp. 4523-4530, vol. 26, Publisher: Nature Publishing Group.
Shan, N., et al., "MiR-153 inhibits migration and invasion of human non-small-cell lung cancer by targeting ADAM19", "Biochemical and Biophysical Research Communications", 2015, pp. 385-391, vol. 456, Publisher: Elsevier.
Soubeyrand, S., et al., "ERK1/2 regulates hepatocyte Trib1 in response to mitochondrial dysfunction", "Biochimica et Biophysica Acta", 2013, pp. 3405-3414, vol. 1833, Publisher: Elsevier.
Soutschek, J., et al., "Therapeutic silencing of an endogenous gene by systemic administration of modified siRNAs", "Nature", Nov. 2004, pp. 173-178, vol. 432, Publisher: Nature Publishing Group.
Tanaka, M., et al., "A Novel RNA-Binding Protein, Ossa/C9orl10, Regulates Activity of Src Kinases to Protect Cells from Oxidative Stress-Induced Apoptosis", "Molecular and Cellular Biology", Jan. 2009, pp. 402-413, vol. 29, No. 2, Publisher: American Society for Microbiology.
Tang, Y., et al., "Rapid induction of apoptosis during Kinesin-5 inhibitor-induced mitotic arrest in HL60 cells", "Cancer Letters", 2011, pp. 15-24, vol. 310, Publisher: Elsevier.
Tanji, C., et al., "A-Kinase Anchoring Protein AKAP220 Binds to Glycogen Synthase Kinase-3 (GSK-3) and Mediates Protein Kinase A-dependent Inhibition of GSK-3", "The Journal of Biological Chemistry", Oct. 4, 2002, pp. 36955-36961, vol. 277, No. 40, Publisher: The American Society for Biochemistry and Moleular Biology, Inc.
Tennakoon, S., et al., "The calcium-sensing receptor and the hallmarks of cancer", "Biochimica et Biophysica Acta", 2016, pp. 1398-1407, Publisher: Elsevier.
Tomari, Y., et al., "Perspective: machines for RNAi", "Genes & Development", 2005, pp. 517-529, vol. 19, Publisher: Cold Spring Harbor Laboratory Press.
Ueno, K., et al., "Tumor suppressor microRNA-493 decreases cell motility and migration ability in human bladder cancer cells downregulating RhoC and FZD4", "Mol Cancer Ther.", Jan. 11, 2012, pp. 244-253, vol. 11, No. 1, Publisher: NIH Public Access.
Van Rooij, E., et al., "Developing MicroRNA Therapeutics", "Circulation Research", 2012, pp. 496-507, vol. 110, Publisher: http://circres.ahajournals.org.
Venere, M., et al., "The Mitotic Kinesin KIF11 is a Central Driver of Invasion, Proliferation, and Self Renewal in Glioblastoma", "Sci Transl Med.", Sep. 9, 2015, p. 304ra143, 1-27, vol. 7, No. 304, Publisher: HHS Public Access.
Whiting, J., et al., "Protein Kinase A Opposes the Phosphorylation-dependent Recruitment of Glycogen Synthase Kinase 3 to A-kinase Anchoring Protein 220", "The Journal of Biological Chemistry", Aug. 7, 2015, pp. 19445-19457, vol. 290, No. 32, Publisher: The American Society for Biochemistry and Molecular Biology.
Wiggins, J., et al., "Development of a lung cancer therapeutic based on the tumor suppressor microRNA-34", "Cancer Res.", Jul. 15, 2010, pp. 5923-5930, vol. 70, No. 17, Publisher: NIH Public Access.
Zhang, L, et al., "Development of transcritomic biomarker signature in human saliva to detect lung cancer", "Cellular and Molecular Life Sciences", 2012, pp. 3341-3350, vol. 69, Publisher: Springer.
Zhang, Q., et al, "Role of microRNA-30c Targeting ADAM19 in Colorectal Cancer", "PLOS ONE", Mar. 23, 2015, pp. 1-14, e0120698, vol. 10, No. 3, Publisher: journal.pone.0120698.
Zheng, C., et al., "microRNA-195 functions as a tumor suppressor by inhibiting CBX4 in hepatocellular carcinoma", "Oncology Reports", 2015, pp. 1115-1122, vol. 33, Publisher: Spandidos Publications UK Ltd.
Zhang, Y., et al., "MicroRNA Expression Profile on Solid Subtype of Invasive Lung Adenocarcinoma Reveals a Panel of Four miRNAs to be Associated with Poor Prognosis in Chinese Patients", "Journal of Cancer", 2016, pp. 1610-1620, vol. 7.

* cited by examiner

DOUBLE-STRANDED OLIGO RNA STRUCTURE COMPRISING MIRNA

CROSS-REFERENCE TO RELATED APPLICATIONS

This application is a U.S. national phase under the provisions of 35 U.S.C. § 371 of International Patent Application No. PCT/KR17/09271 filed Aug. 24, 2017, which in turn claims priority under 35 U.S.C. §119 of Korean Patent Application No. 10-2016-0107937 filed Aug. 24, 2016. The disclosures of such international patent application and Korean priority patent application are hereby incorporated herein by reference in their respective entireties, for all purposes.

TECHNICAL FIELD

The present invention relates to a double-stranded oligo RNA structure containing double-stranded miRNA and a composition for preventing or treating cancer containing the same. More specifically, the present invention relates to an anti-cancer pharmaceutical composition containing a double-stranded oligo RNA structure comprising miR-3670, miR-4477a and miR-8078, effectively inhibiting proliferation of cancer cells or inducing apoptosis of cancer cells, and a pharmaceutically acceptable carrier.

BACKGROUND ART

Surgical removal of tumors has been used as an effective and traditional treatment method for diseases caused by failure of normal control of genes, which are typically referred to as cancer. However, when primary cancer metastasizes to other organs, anticancer drug therapy is used due to impossibility of surgical operation. Anticancer drugs used for drug therapy are generally monomolecular substances synthesized by an organic or inorganic method. Anticancer drugs have been developed and used in order to inhibit activities of proteins by effectively binding to the proteins that disrupt signal transduction pathways through over-expression of phosphorylation factor proteins contained in signal transduction pathways. Such traditional drug therapy involves many side effects, which include that the substance used as a drug is an artificially synthesized exogenous substance and that actions of anticancer substances target already over-expressed proteins.

The development of drug therapies to replace the traditional drug treatment methods has progressed in many ways, one of which is the use of small interfering RNAs (hereinafter referred to as "siRNAs"). (Iorns, E., Lord, C. J., Turner, N. & Ashworth, A. Utilizing RNA interference to enhance cancer drug discovery. Nat Rev Drug Discov 6, 556-68. 2007.). siRNAs are single-stranded RNAs including 16 to 27 nucleotides, which act as constituent components of ribonucleoproteins known as RISCs (RNA Induced Silencing complexes) (Tomari, Y. & Zamore, P. D. Perspective: machines for RNAi. Genes Dev 19, 517-29, 2005, Chu, C. Y. & Rana, T. M. Potent RNAi by short RNA triggers. Rna 14, 1714-9, 2008, Mittal, V. Improving the efficiency of RNA interference in mammals. Nat Rev Genet 5, 355-65, 2004, Reynolds, A. et al. Rational siRNA design for RNA interference. Nat Biotechnol 22, 326-30. 2004). RISCs function as RNA enzyme scissors, that is, RISCs cleave messenger RNAs (hereafter referred to as "mRNAs") to inhibit the production of proteins from mRNAs. The siRNAs contained in RISCs bind to mRNAs having sequences complementary to the siRNAs sequences to form double-stranded RNAs. The RISCs act as RNA enzyme scissors to cleave the target mRNAs, thus preventing mRNAs from acting as templates to repeatedly produce proteins.

Such siRNA-based anti-cancer agents are considered to be more advanced than the above-mentioned anticancer agents in that the siRNA-based anti-cancer agents block mRNAs before protein production and use RNAs and intracellular RISC systems. However, there are side effects called "off-target effects" that cannot be solved by siRNA-based technologies (Jackson, A. L. et al. Widespread siRNA "off-target" transcript silencing mediated by seed region sequence complementarity. Rna 12, 1179-87, 2006., Jackson, A. L. et al. Position-specific chemical modification of siRNAs reduces "off-target" transcript silencing. Rna 12, 1197-205, 2006., Jackson, A. L. et al. Expression profiling reveals off-target gene regulation by RNAi. Nat Biotechnol 21, 635-7, 2003., Nielsen, C. B. et al. Determinants of targeting by endogenous and exogenous microRNAs and siRNAs. Rna 13, 1894-910, 2007., Peek, A. S. & Behlke, M. A. Design of active small interfering RNAs. Curr Opin Mol Ther 9, 110-8, 2007.). As described above, siRNA-based anti-cancer agents degrade mRNAs that bind complementarily to siRNA sequences. However, the siRNA-based anti-cancer agents bind to even mRNAs which are not complementary to the entirety of siRNA sequences and are complementary to the part thereof, thus causing degradation, which is called a "off-target effect", meaning causing degradation of non-target mRNAs.

In order to overcome technical difficulties of the aforementioned siRNA-based anticancer drugs, research is underway to use microRNAs (hereinafter referred to as miRNAs) as therapeutic agents (Agostini, M. & Knight, R. A. miR-34: from bench to bedside. Oncotarget 5, 872-81, 2014., van Rooij, E., Purcell, A. L. & Levin, A. A. Developing MicroRNA Therapeutics. Circulation Research 110, 496-507, 2012., Burnett, J. C. & Rossi, J. J. RNA-based therapeutics: current progress and future prospects. Chem Biol 19, 60-71, 2012., Dangwal, S. & Thum, T. microRNA therapeutics in cardiovascular disease models. Annu Rev Pharmacol Toxicol 54, 185-203, 2014.). miRNAs are RNAs composed of 16 to 27 nucleotides, which are classified as protein non-coding RNAs as compared to messenger RNAs (mRNAs) that are translated into proteins (Carthew, R. W. & Sontheimer, E. J. Origins and Mechanisms of miRNAs and siRNAs. Cell 136, 642-55, 2009., MacFarlane, L. A. & Murphy, P. R. MicroRNA: Biogenesis, Function and Role in Cancer. Current Genomics 11, 537-561, 2010., Bartel, D. P. MicroRNAs: target recognition and regulatory functions. Cell 136, 215-33, 2009.). miRNAs are recorded in the genomes of higher plant and animal cells and are known to play a key role in regulating cell metabolism and functions, including cell production, growth, differentiation and death. To date, about 2,000 types of miRNAs have been found in the human genome, the function of many of these miRNAs are still unknown.

miRNAs are transcribed from the genomes into RNAs by an RNA polymerase called "Pol II", the initial length of which is too variable to be specified (Carthew, R. W. & Sontheimer, E. J. Origins and Mechanisms of miRNAs and siRNAs. Cell 136, 642-55, 2009., Brodersen, P. & Voinnet, O. Revisiting the principles of microRNA target recognition and mode of action. Nat Rev Mol Cell Biol 10, 141-148, 2009.). This is due to the diversity of the location of the miRNA in the genome. That is, miRNA is produced in many ways, for example, miRNA is located in an intron, which is a part not involved in the protein production of mRNAs, and is transcribed at the same time as in production of mRNAs, or miRNA is located in the intergenic region on the genome and is transcribed independently (Malone, C. D. & Hannon, G. J. Small RNAs as guardians of the genome. Cell 136, 656-68, 2009.). miRNA produced at an early stage is called "primary microRNA", and the primary miR is edited into the precursor miRNA (precursor miRNA, pre-miR) by an RNA-cleaving enzyme (RNase) called "Drosha" in the nucleus (Bartel, D. P. MicroRNAs: target recognition and regulatory functions. Cell 136, 215-33, 2009.). Pre-miR has an RNA hairpin structure consisting of approximately 70 to 80 nucleotides. Pre-miR inside the cell nucleus is transported from the nucleus to the cytoplasm by exportin proteins, and is secondarily processed by another RNA-cleaving enzyme (RNase) called "Dicer" in the cytoplasm to produce double-stranded mature microRNAs (hereinafter referred to as "miRs" without any other modifiers) composed of 16 to 27 nucleotides. RNA of one strand of the double-stranded miRs is selectively determined, has activity by binding to the ribonucleoprotein complex, RISC, and binds to the target mRNA using the miR sequence.

In general, mRNAs can be divided into three parts based on involvement in protein production. That is, mRNAs can be divided into a coding region having protein translation information, and the 5' and 3' parts of the coding region having no protein translation information, respectively, 5'-UTR (untranslated region) and 3'-UTR. siRNAs, which cause degradation of target mRNAs using complementary sequences, act regardless of the 5'-UTR, 3'-UTR and coding parts of the mRNA, whereas miRs bind primarily to the 3'-UTR ((Carthew, R. W. & Sontheimer, E. J. Origins and Mechanisms of miRNAs and siRNAs. Cell 136, 642-55, 2009., Bartel, D. P. MicroRNAs: target recognition and regulatory functions. Cell 136, 215-33, 2009.).

The unique features of miRNAs distinguished from siRNAs, in addition to their binding sites to the mRNAs, are that the siRNAs bind primarily to mRNAs containing sequences complementary to the entire siRNA sequence, while, regarding the miRNAs, seed region sequences with a limited size, located at nucleotides at positions of 2 to 8 from the 5' end, are mainly used to recognize target mRNAs, so the sequence of the entire miRNA does not have a perfectly complementary sequence with the target gene, and although it contains even a part of the non-complementary sequence, it does not affect miRNA activity (Bartel, D. P. MicroRNAs: target recognition and regulatory functions. Cell 136, 215-33, 2009.). Since the sequence size of the seed region is 6 to 8 nucleotides, there are various mRNA types having the sequence complementary thereto in the 3' UTR. For this reason, it is possible to simultaneously control several types of mRNAs with one type of miRNA. The properties of these miRNAs impart, to miRNAs, functions as efficient regulators that are involved in controlling various cell physiological properties that entail cell division, growth, differentiation and death. In addition, the functions of miRNAs as regulators are advantageous in achieving effective anticancer effects because siRNAs target the suppression of single gene expression, while miRNAs simultaneously inhibit the expression of many cancer-inducing genes.

A large number of mRNAs contain portions of the 3' UTR to which one or more types of miRNAs are likely to bind, and one bioinformatic calculation shows that protein production of approximately 30% of the total mRNA is regulated by miRNAs.

The fact that miRNAs act as major regulators in signaling pathways of mRNAs can be identified in that they play a key role in major diseases including cancer (MacFarlane, L.-A. & Murphy, P. R. MicroRNA: Biogenesis, Function and Role in Cancer. Current Genomics 11, 537-561. 2010., Malone, C. D. & Hannon, G. J. Small RNAs as guardians of the genome. Cell 136, 656-68. 2009., Nicoloso, M. S., Spizzo, R., Shimizu, M., Rossi, S. & Calin, G. A. MicroRNAs--the micro steering wheel of tumour metastases. Nat Rev Cancer 9, 293-302. 2009., Landi, D., Gemignani, F. & Landi, S. Role of variations within microRNA-binding sites in cancer. Mutagenesis 27, 205-10. 2012.). In fact, several studies have shown that expression patterns of miRNAs in cancer cells differ greatly from the expression patterns of miRNAs in normal cells. In addition, there is a great difference in miRNA expression patterns depending on the primary organs in which cancer occurs. Various types of cancers such as lung cancer, liver cancer, skin cancer and blood cancer have unique miRNA expression patterns, which indicates that miRNAs have a pivotal role in cancer biology. In particular, the levels of miRNAs expressed in carcinomas are known to be generally lower than levels of miRNAs expressed in normal cells.

Recently, attempts have been made to use miRNAs as therapeutic agents based on the aforementioned close correlation of miRNAs with cancer. For example, clinical testing is underway to identify the ability of miRNAs called "miR-34a" to inhibit proliferation of cancer cells and induce apoptosis (Wiggins, J. F. et al. Development of a lung cancer therapeutic based on the tumor suppressor microRNA-34. Cancer Res 70, 5923-30. 2010., Bader, A. G. et al. miR-34 Regulated Genes and Pathways as Targets for Therapeutic Intervention. Google Patents, 2009., Hermeking, H. The miR-34 family in cancer and apoptosis. Cell Death Differ 17, 193-9. 2010., Chang, T. C. et al. Transactivation of miR-34a by p53 broadly influences gene expression and promotes apoptosis. Mol Cell 26, 745-52. 2007.).

In order to use miRNA as an anticancer agent, there is a need for an effective method for transferring miRNAs injected from the outside of the living body to pathological tissues without degradation of miRNAs in the living body. For this purpose, RNA oligo structures containing miRNA sequences can be used. It is known that a high efficiency can be induced in vivo by linking a chemical substance or the like to the terminal site of RNA oligos so as to provide enhanced pharmacokinetic characteristics (Nature 11; 432 (7014):173-8, 2004). The stability of the RNA oligos depends on the nature of chemical substance bound to the ends of sense (passenger) or antisense (guide) strands of RNA oligos. For example, an RNA oligo, which is conjugated with a polymer compound such as polyethylene glycol (PEG), interacts with an anionic phosphate group of oligo in the presence of a cationic substance to form a complex, which can become a carrier with improved stability (J Control Release 129 (2): 107-16, 2008). In particular, micelles composed of polymer complexes are extremely small in size, very uniform in distribution and are spontaneously formed, as compared with other systems used as drug delivery carriers, such as microspheres or nanoparticles, thus having advantages of easy quality control of preparations and reproducibility.

Further, in order to improve intracellular delivery efficiency of RNA oligos, techniques for securing the stability of oligos and for securing efficient cell membrane permeability through oligo conjugates wherein RNA oligos are simply bonded to a hydrophilic substance (polyethylene glycol (PEG)) as a biocompatible polymer via a simple covalent bond or a linker-mediated covalent bond have been developed (Korean Patent No. 10-0883471). However, chemical modification of oligo and conjugation of polyethylene glycol (PEG) still do not solve the drawbacks of low in vivo stability and non-favorable delivery to target organs. In order to solve these drawbacks, double-stranded oligo RNA structures in which hydrophilic and hydrophobic substances are bonded to double-stranded oligo RNAs have been developed. These structures form self-assembled nanoparticles called "SAMiRNA™" (self-assembled micelle inhibitory RNAs) via hydrophobic interaction of hydrophobic substances (See Korean Patent No. 10-1224828), and this SAMiRNA™ technology has advantages of obtaining much smaller and more homogenous nanoparticles than conventional delivery technologies.

Under these technical backgrounds, as a result of efforts to find miRNAs with excellent efficacies to inhibit proliferation of cancer cells and induce death of cancer cells, the present inventors found miR-3670, miR-4477a and miR-3477a with excellent anticancer efficacy, and identified that these miRNAs and double-stranded oligo RNA structures containing the same effectively inhibited the expression of a number of genes known as cancer-inducing genes to achieve anticancer effects, thus completing the present invention.

DISCLOSURE

Technical Problem

It is an object of the present invention to find miRNAs with excellent efficacies to inhibit proliferation of cancer cells and induce death of cancer cells, and provide double-stranded oligo RNA structures containing the same and a composition for preventing or treating cancer containing the same as an active ingredient.

Technical Solution

To accomplish the object, the present invention provides a double-stranded oligo RNA structure comprising the following Formula (1):

A-X-R-Y-B   Formula (1)

wherein A represents a hydrophilic material, B represents a hydrophobic material, X and Y each independently represent a simple covalent bond or a linker-mediated covalent bond, and R represents at least one miRNA selected from the group consisting of miR-3670, miR-4477a, and miR-8078.

The present invention also provides a composition for preventing or treating cancer comprising the oligonucleotide structure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE

Unless defined otherwise, all technical and scientific terms used herein have the same meaning as those appreciated by those skilled in the field to which the present invention pertains. In general, nomenclature used herein is well-known in the art and is ordinarily used.

According to the present invention, miRNAs having better efficacies than miR-34a known to have anticancer effects are found and anti-cancer effects thereof are identified.

According to the present invention, 1,700 types of miRNA screening libraries are synthesized (Example 1), NCI-H460 (lung cancer cell line) cells are treated with the miRNA screening libraries, and the ability to suppress growth of cancer cells is measured, as a result, miR-3670, miR-4477a and miR-8078 having the following base sequences (Table 3) have found to have better efficacies than miR-34a, so that it is identifed that miR-3670, miR-4477a and miR-8078 have excellent anticancer efficacies (FIGS. 4 to 8).

Accordingly, the present invention is directed to a double-stranded oligo RNA structure that comprises at least one miRNA selected from the group consisting of miR-3670, miR-4477a and miR-8078, and the structure represented by the following Formula (1):

A-X-R-Y-B   Formula (1)

wherein A represents a hydrophilic material, B represents a hydrophobic material, X and Y each independently represent a simple covalent bond or a linker-mediated covalent bond, and R represents at least one miRNA selected from the group consisting of miR-3670, miR-4477a, and miR-8078.

According to the present invention, miR-3670 may be a double stranded RNA comprising a base sequence of SEQ ID NO. 35; and a base sequence of SEQ ID NO. 36 or SEQ ID NO. 67.

According to the present invention, miR-4477a may be a double stranded RNA comprising a base sequence of SEQ ID NO. 43; and a base sequence of SEQ ID NO. 44 or SEQ ID NO. 68.

According to the present invention, miR-8078 may be a double stranded RNA comprising a base sequence of SEQ ID NO. 65; and a base sequence of SEQ ID NO. 66 or SEQ ID NO. 69.

That is, the template strand of miR-3670 may be represented by SEQ ID NO. 35.

```
                      (MIMAT0018093. SEQ ID NO. 35)
5'-AGAGCUCACAGCUGUCCUUCUCUA-3'
``` miRNAs are ultimately active in vivo as single-strands, but should be fed into cells in the form of double strands with a base sequence having a similar base size for binding to RISC. At this time, the antisense binding to the active sequence has a complementary sequence to the active sequence. The complementary sequence has a perfect complementary sequence or an in vivo endogenous sequence. All sequences having double strands or bases located at 3' of one strand may not have a base bond with an opposite (the other) sequence, which is referred to as a 3' overhang. That is, the perfect complementary sequence of miR-3670 is represented by SEQ ID NO. 36.

```
                                      (SEQ ID NO. 36)
5'-GAGAAGGACAGCUGUGAGCUCUUU-3'
```

In addition, the endogenous complementary sequence of miR-3670 may be represented by SEQ ID NO. 67.

```
                                      (SEQ ID NO. 67)
5'-GACUGGUAUAGCUGCUUUUGGAGCCUCA-3'
```

As described in the Background, the seed region corresponding from the $2^{nd}$ base to the $8^{th}$- $9^{th}$ bases of miRNA active sequences are major active factors, and long double strands containing the same may be produced and used upon the production of double stranded RNAs.

Like miR-3670, active sequences of miR-4477a and miR-8078 and complementary sequences that form double strands with the active sequences are represented as follows. As described above, these double strands may include a 3' overhang and may be double strands with a long sequence including the seed region.

```
miR-4477a
                      (MIMAT0019004 SEQ ID NO. 43)
5'-CUAUUAAGGACAUUUGUGAUUC-3'

Perfect complementary sequence of miR-4477a
                                      (SEQ ID NO. 44)
5'-AUCACAAAUGUCCUUAAUAGUU-3'

Endogenous complementary sequence of miR-4477a
                                      (SEQ ID NO. 68)
5'-AUCACAAAUGUCCUUAAUGGCA-3' miR-8078
                      (MIMAT0031005, SEQ ID NO. 65)
5'-GGUCUAGGCCCGGUGAGAGACUC
```

```
Perfect complementary sequence of miR-8078
                                      (SEQ ID NO. 66)
5'-GUCUCUCACCGGGCCUAGACCUU Endogenous complementary sequence of miR-8078
                                      (SEQ ID NO. 69)
5'-CUCCACCGGGCUGACCGGCCUG-3'
```

The miRNAs discovered through the library screening according to the present invention were found to provide anticancer efficacies by controlling genes commonly known to play a key role in the induction, production and growth of cancer. The feature of miRNAs is that one type of miRNA can simultaneously control expression of a plurality of mRNAs. This feature can be identified by the present invention as well and is useful for the development of oligo-based anti-cancer drugs.

Figure 6:
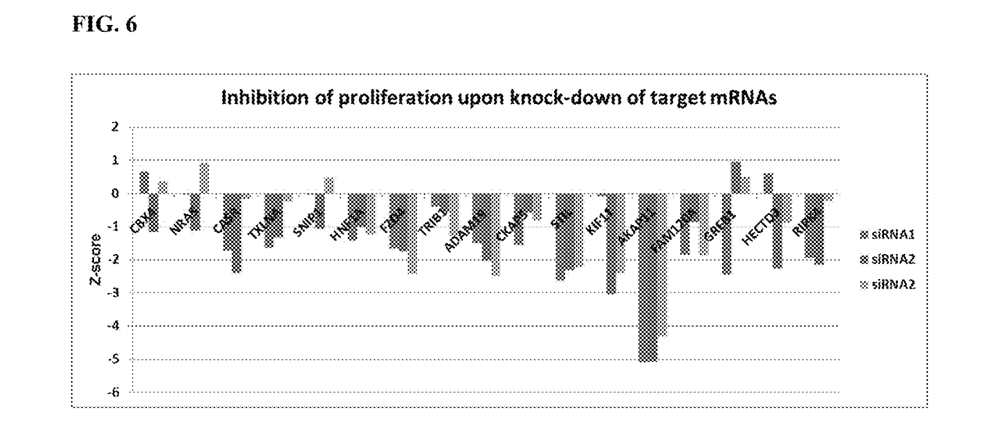
FIG. 6 shows cell death performance represented by Z-score when selecting target candidate groups using the miRNA target prediction software, TargetScan, and reducing the intracellular content using siRNAs targeting the target candidate groups.

The miR-3670 of the present invention simultaneously inhibits expressions of CBX4, NRAS, CASR, TXLNA, SNIP1, HNF1A, FZD4, TRIB1, ADMA19 and CKAP5, miR-8078 inhibits expressions of GREB1, HECTD3 and RIPK4, and miR-4477a simultaneously inhibits expressions of STIL, KIF11, AKAP11, and FAM120A (FIG. 6).

The target genes inhibited by miRNAs of the present invention are known to have the following functions.

CBX4 (polycomb chromobox 4) is involved in angiogenesis of tumors and facilitation of metastasis thereof, and NRAS is known to play a key role in tumor growth and cell division (Orouji, E. et al. MAP Kinase pathway gene copy alterations in NRAS/BRAF wild-type advanced melanoma. Int J Cancer (2015); Zheng, C. et al. MicroRNA-195 functions as a tumor suppressor by inhibiting CBX4 in hepatocellular carcinoma. Oncol Rep 33, 1115-22 (2015); Jiao, H. K. et al. Prognostic significance of Cbx4 expression and its beneficial effect for transarterial chemoembolization in hepatocellular carcinoma. Cell Death Dis 6, e1689 (2015); Ohashi, K. et al. Characteristics of lung cancers harboring NRAS mutations. Clin Cancer Res 19, 2584-(2013)).

CASR is found to be over-expressed in tumors and is required for metastasis of tumors, and TXLNA is known to be involved in the growth and metastasis of tumors. Clinical results have been reported that the survival rate of patients with high expression rates of TXLNA is low (Mashidori, T., Shirataki, H., Kamai, T., Nakamura, F. & Yoshida, K. Increased alpha-taxilin protein expression is associated with the metastatic and invasive potential of renal cell cancer. Biomed Res 32, 103-10 (2011); Tennakoon, S., Aggarwal, A. & Kallay, E. The calcium-sensing receptor and the hallmarks of cancer. Biochim Biophys Acta (2015); Ohtomo, N. et al. Expression of alpha-taxilin in hepatocellular carcinoma correlates with growth activity and malignant potential of the tumor. Int J Oncol 37, 1417-23 (2010)).

SNIP1, known as a transcriptional coactivator, promotes the expression of cyclin D1, which is essential for cell growth and division. It is known that the anticancer prognosis of patients with a high expression level of SNIP1 is bad. In addition, SNIP1 is known to function to promote tumor growth in combination with c-Myc, which acts as a major regulator of cell proliferation (Li, Q. et al. SNIP1: a new activator of HSE signaling pathway. Mol Cell Biochem 362, 1-6 (2012); Fujii, M. et al. SNIP1 is a candidate modifier of the transcriptional activity of c-Myc on E box-dependent target genes. Mol Cell 24, 771-83 (2006); Roche, K. C., Rocha, S., Bracken, C. P. & Perkins, N. D. Regulation of ATR-dependent pathways by the FHA domain containing protein SNIP1. Oncogene 26, 4523-30 (2007);

Jeon, H. S. et al. High expression of SNIP1 correlates with poor prognosis in non-small cell lung cancer and SNIP1 interferes with the recruitment of HDAC1 to RB in vitro. Lung Cancer 82, 24-30 (2013); Liang, X. et al. Hypoxia-inducible factor-1 alpha, in association with TWIST2 and SNIP1, is a critical prognostic factor in patients with tongue squamous cell carcinoma. Oral Oncol 47, 92-7 (2011)).

HNF1A and FZD4 are constituent factors of the Wnt signaling system that is deeply involved in the growth and survival of tumors. The Wnt signaling system has been intensively researched in tumor biology and its importance is widely known. TRIB1 is known to play a role in growth and metastasis of tumor cells and inhibition of cell apoptosis, and is known as a factor regulating the MAPK signaling system which is one of the main signaling pathways of tumor growth (Pecina-Slaus, N. et al. Wnt signaling transcription factors TCF-1 and LEF-1 are upregulated in malignant astrocytic brain tumors. Histol Histopathol 29, 1557-64 (2014); Ueno, K. et al. Tumor suppressor microRNA-493 decreases cell motility and migration ability in human bladder cancer cells by downregulating RhoC and FZD4. Mol Cancer Ther 11, 244-53 (2012); Lin, Z. Y. et al. MicroRNA-224 inhibits progression of human prostate cancer by downregulating TRIB1. Int J Cancer 135, 541-50 (2014); Soubeyrand, S., Naing, T., Martinuk, A. & McPherson, R. ERK1/2 regulates hepatocyte Trib1 in response to mitochondrial dysfunction. Biochim Biophys Acta 1833, 3405-14 (2013)).

ADAM19 is a protein distributed on the cell membrane, which is known to play diverse biological roles including cell-cell contact and cell-extracellular matrix contact. It is known in tumor biology that ADAM19 is strongly correlated with growth and metastasis of tumors. The CKAP5 gene, which is known to play a key role in the survival of tumors through functional genetic screens, is also controlled by the miRNA, which is identified by the present invention. GREB1, which is a gene related to signaling pathways of hormone-responsive tissues or tumors, is known to be overexpressed in various types of tumors to promote cell growth (Zhang, Q. et al. Role of microRNA-30c targeting ADAM19 in colorectal cancer. PLoS One 10, e0120698 (2015); Shan, N., Shen, L., Wang, J., He, D. & Duan, C. MiR-153 inhibits migration and invasion of human non-small-cell lung cancer by targeting ADAM19. Biochem Biophys Res Commun 456, 385-91 (2015); Martens-de Kemp, S. R. et al. Functional genetic screens identify genes essential for tumor cell survival in head and neck and lung cancer. Clin Cancer Res 19, 1994-2003 (2013); Rae, J. M. et al. GREB1 is a novel androgen-regulated gene required for prostate cancer growth. Prostate 66, 886-94 (2006); Zhang, L. et al. Development of transcriptomic biomarker signature in human saliva to detect lung cancer. Cell Mol Life Sci 69, 3341-50 (2012); Laviolette, L. A., Hodgkinson, K. M., Minhas, N., Perez-Iratxeta, C. & Vanderhyden, B. C. 17beta-estradiol upregulates GREB1 and accelerates ovarian tumor progression in vivo. Int J Cancer 135, 1072-84 (2014)).

HECTD3 is known as an E3 ubiquitin ligase that inhibits tumor death by inducing degradation of caspase-8 by attaching polyubiquitin to caspase-8 which facilitates cell apoptosis and increases drug resistance to cisplatin anticancer drugs by stabilizing MALT1 proteins. RIPK4 has been reported as receptor-interacting protein kinase 4 to induce accumulation of β-catenin, which is a cell growth signaling factor, and to activate the Wnt signaling system. It has been found that artificial elimination of RIPK4 can inhibit tumor growth in tumor animal models (Li, Y. et al. The HECTD3 E3 ubiquitin ligase facilitates cancer cell survival by promoting K63-linked polyubiquitination of caspase-8. Cell Death Dis 4, e935 (2013); Li, Y. et al. The HECTD3 E3 ubiquitin ligase suppresses cisplatin-induced apoptosis via stabilizing MALT1. Neoplasia 15, 39-48 (2013); Huang, X. et al. Phosphorylation of Dishevelled by protein kinase RIPK4 regulates Wnt signaling. Science 339, 1441-5 (2013)).

The STIL gene as an essential element in the transition from the G2 phase to the M phase during the cell cycle is observed to be highly expressed in various types of cancer and is known to be necessary for tumor proliferation and survival. KIF11 is also reported to be one of factors necessary for the growth and metastasis of tumor cells and is known to inhibit growth of tumors by inhibiting the activity of KIF11 (Erez, A. et al. Sil overexpression in lung cancer characterizes tumors with increased mitotic activity. Oncogene 23, 5371-7 (2004); Erez, A. et al. The SIL gene is essential for mitotic entry and survival of cancer cells. Cancer Res 67, 4022-7 (2007); Tang, Y., Orth, J. D., Xie, T. & Mitchison, T. J. Rapid induction of apoptosis during Kinesin-5 inhibitor-induced mitotic arrest in HL60 cells. Cancer Lett 310, 15-24 (2011); Venere, M. et al. The mitotic kinesin KIF11 is a driver of invasion, proliferation, and self-renewal in glioblastoma. Sci Transl Med 7, 304ra143 (2015)).

AKAP11, which binds to protein kinase A (PKA) to increase PKA activity, simultaneously binds to GSK-3beta as well to promote phosphorylation of GSK-3beta by PKA. Phosphorylated GSK-3beta loses its activity, which is recognized as a signal that stimulates growth in cells and is one of the major mechanisms leading to tumor growth. Tumor cells are exposed to a variety of stress conditions such as acidic conditions and oxygen deficiency conditions. Under these severe conditions, the mechanism of tumor cell death is maintained. Among them, FAM120A, which is an RNA binding protein, is known to activate a kinase such as Src, thereby increasing inhibition of cell death and resistance to drugs (Logue, J. S. et al. AKAP220 protein organizes signaling elements that impact cell migration. J Biol Chem 286, 39269-(2011); Whiting, J. L. et al. Protein Kinase A Opposes the Phosphorylation-dependent Recruitment of Glycogen Synthase Kinase 3beta to A-kinase Anchoring Protein 220. J Biol Chem 290, 19445-57 (2015); Tanji, C. et al. A-kinase anchoring protein AKAP220 binds to glycogen synthase kinase-3beta (GSK-3beta) and mediates protein kinase A-dependent inhibition of GSK-3beta. J Biol Chem 277, 36955-61 (2002); Tanaka, M. et al. A novel RNA-binding protein, Ossa/C9orf10, regulates activity of Src kinases to protect cells from oxidative stress-induced apoptosis. Mol Cell Biol 29, 402-13 (2009); Bartolome, R. A. et al. IL13 Receptor alpha2 Signaling Requires a Scaffold Protein, FAM120A, to Activate the FAK and PI3K Pathways in Colon Cancer Metastasis. Cancer Res 75, 2434-44 (2015)).

Figure 7:
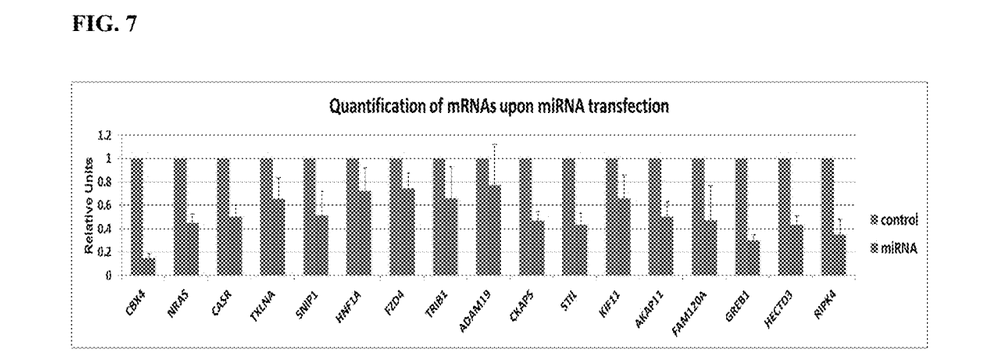
FIG. 7 shows results of qPCR analysis indicating the degree of inhibition of expression levels of genes identified in FIG. 6 by miRNA.
Figure 8:
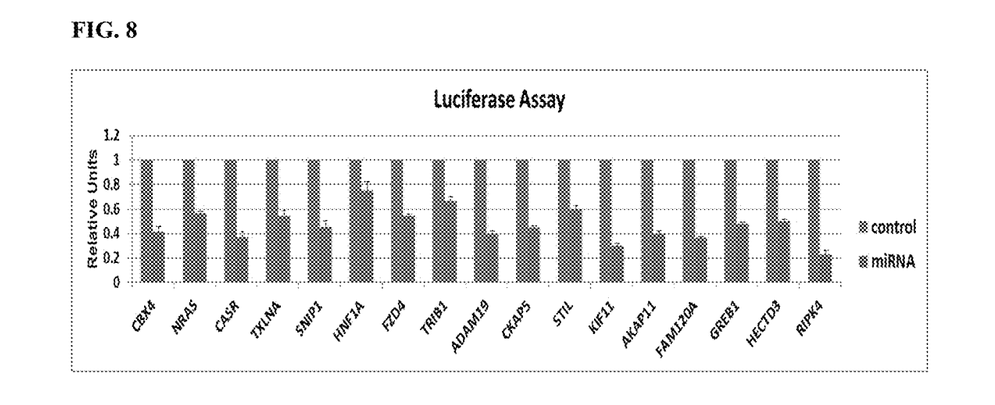
FIG. 8 shows the degree of inhibition against the expression of luciferase proteins by miRNAs by cloning the genes identified in FIG. 6 on the 3' UTR of luciferase.

It was identified by the present invention that, when contents of genes in cells were reduced using siRNAs, the growth of the cells was decreased as in the case of using miR-3670, miR4477a and miR-8078 (FIG. 6). qPCR results showed that, when miR-3670, miR-4477a and miR-8078 were delivered into lung cancer cells, the mRNA expression of the genes was decreased (FIG. 7). In addition, luciferase results identified that the genes were direct targets of miR-3670, miR-4477a and miR-8078 (FIG. 8). This indicates that miR-3670, miR-4477a and miR-8078 induce death of tumor cells by directly and simultaneously inhibiting the expression of several genes important for growth and survival of tumor cells.

Among the miRNAs, miR-3670 simultaneously inhibits expression of CBX4, NRAS, CASR, TXLNA, SNIP1, HNF1A, FZD4, TRIB1, ADMA19 and CKAPS, miR-8078 inhibits expression of GREB1, HECTD3 and RIPK4, and miR-4477a simultaneously inhibits expression of STIL, KIF11, AKAP11 and FAM120A. For this reason, the mRNAs of the genes include a perfect match wherein the corresponding miRNA regions are complementary 100% to base sequences, as well as mismatch wherein the corresponding miRNA regions are inconsistent with some base sequences. For these miRNAs, the match of the seed regions is the most important, and miRNAs preferably have at least 70%, more preferably at least 80%, even more preferably at least 90%, still even more preferably 95% or more, and most preferably 100%, of an identity with a part of mRNA sequences of the corresponding genes.

Such miRNAs may be duplexes, include single molecule polynucleotide, and be antisense oligonucleotides or microRNAs (miRNAs), but are not limited thereto.

With regard to the oligo conjugates, wherein hydrophilic and hydrophobic mateirals are bound to RNA oligos, according to the present invention, the conjugates, wherein hydrophilic and hydrophobic materials are bound to both ends of RNA oligos, can efficiently deliver RNA oligos in vivo and improve stability.

Self-assembled nanoparticles are formed through hydrophobic interactions of hydrophobic materials. These nanoparticles have extremely excellent in vivo delivery efficiency and in vivo stability, and the improvement in structures provides very uniform particle sizes and easy quality control (QC), thus having an advantage of simple drug manufacturing process.

In one embodiment, the hydrophilic material in the double-stranded oligo RNA structures comprising miRNAs according to the present invention is represented by $(A)_n$, $(A_m\text{-}J)_n$ or $(J\text{-}A_m)_n$, wherein A represents a hydrophilic material monomer, n represents 1 to 200, m represents 1 to 15, and J represents a linker that links m hydrophilic material monomers to one another, or links m hydrophilic material monomers to oligonucleotides.

When the hydrophilic substance is $(A)_n$, the double-stranded oligo RNA structure according to the present invention has the structure represented by the following Formula (1'):

[Formula (1')]

wherein A, B, X and Y are as defined in Formula (1), S represents a sense strand of specific miRNA regarding the corresponding gene and AS represents an antisense strand of specific miRNA regarding the corresponding gene.

In one embodiment, the double-stranded oligo RNA structure comprising miRNAs according to the present invention may be a double-stranded oligo RNA structure comprising the structure represented by the following Formula (2):

A-X-5'R3'Y-B [Formula (2)]

wherein A, B, X, Y and R are as defined in Formula (1).

More preferably, the double-stranded oligo RNA structure has a structure represented by the following Formula (2'):

[Formula (2')]

In one embodiment, the hydrophilic material may be a cationic or non-ionic polymer material having a molecular weight of 200 to 10,000, preferably a non-ionic polymer substance having a molecular weight of 1,000 to 2,000. As the hydrophilic material, a non-ionic hydrophilic polymer compound, for example, polyethylene glycol, polyvinylpyrrolidone or polyoxazoline is preferably used, but the present invention is not limited thereto.

In another embodiment, when the hydrophilic substance is $(Am\text{-}J)_n$ or $(J\text{-}A_m)_n$, the double-stranded oligo RNA structure according to the present invention has a structure represented by the following Formula (3) or Formula (4):

$(A_m\text{-}J)_n$-X-R-Y-B [Formula (3)]

$(J\text{-}A_m)_n$-X-R-Y-B [Formula (4)]

In Formula (3) and Formula (4), A represents a hydrophilic material monomer, n represents 1 to 200, represents 1 to 15, J represents a linker that links m hydrophilic material monomers to one another, or links m hydrophilic material monomer to oligonucleotide, X and Y each independently represent a simple covalent bond or a linker-mediated covalent bond, and R represents specific miRNA according to the present invention. More preferably, the double-stranded oligo RNA structure comprising miRNA according to the present invention may have a structure represented by Formula (3'):

$(A_m\text{-}J)_n$-X-S-Y-B

[Formula (3')]

wherein A, B, J, m, n, X and Y are as defined in Formula (3), S represents a sense strand of specific miRNA regarding the corresponding gene, and AS represents an antisense strand of specific miRNA regarding the corresponding gene.

More preferably, the double-stranded oligo RNA structure comprising miRNAs according to the present invention has a structure represented by the following Formula (4'):

$(J\text{-}A_m)_n$-X-S-Y-B AS [Formula (4')]

wherein A, B, J, m, n, X and Y are as defined in Formula (4), S represents a sense strand of specific miRNA regarding the corresponding gene, and AS represents an antisense strand of specific miRNA regarding the corresponding gene.

Any monomer of non-ionic hydrophilic polymers may be used as the hydrophilic material monomer (A) in Formula (3) and Formula (4) without particular limitation so long as it satisfies the objects of the present invention. Preferred is a monomer selected from Compounds (1) to (3) shown in Table 1, and more preferred is a monomer of Compound (1). Gin Compound (1) is preferably selected from $CH_2$, O, S and NH.

In particular, among the hydrophilic material monomers, the monomer represented by compound (1) has advantages of having a variety of functional groups which would be introduced, exhibiting excellent bio-compatibility, for example, providing better in vivo affinity and inducing less immune reactions, and improving in vivo stability and delivery efficiency of oligonucleotide contained in the structure according to Formula (3) and Formula (4), thus being very suitable for the manufacture of the structure according to the present invention.

TABLE 2

Preferred hydrophilic material monomer structures according to the present invention

| Compound (1) | Compound (2) | Compound (3) |
| --- | --- | --- |
|  G is $CH_2$, O, S or NH |  |  |

The hydrophilic material in Formula (3) and Formula (4) preferably has a total molecular weight of 1,000 to 2,000. Accordingly, for example, wherein hexaethylene glycol in Compound (1), that is, G is O, and m is 6, is used in Formula (3) and Formula (4), the molecular weight of the hexaethylene glycol spacer is 344 and thus the number of repeats (n) is preferably 3 to 5. According to the present invention, in Formula (3) and Formula (4), a repeat unit represented by $(A_m-J)$ or $(J-A_m)$, that is, a hydrophilic material block may be used as an appropriate number represented by "n". A, the hydrophilic material monomer and J, the linker, contained in each hydrophilic material block, may be independently identical or different between the hydrophilic material blocks. That is, when three hydrophilic material blocks are used (n=3), different hydrophilic material monomers may be used for all the hydrophilic material blocks, for example, the hydrophilic material monomer according to Compound (1) may be used for the first block, the hydrophilic material monomer according to Compound (2) may be used for the second block, and the hydrophilic material monomer according to Compound (3) may be used for the third block. Alternatively, any one hydrophilic material monomer selected from hydrophilic material monomers according to Compounds (1) to (3) may be used for all hydrophilic material blocks. Similarly, the linker, which mediates the bond between the hydrophilic material monomers, used for respective hydrophilic material blocks, may be identical or different. In addition, m, the number of the hydrophilic material monomers, may be identical or different for the respective hydrophilic material blocks. That is, different numbers of hydrophilic material monomers may be used, for example, for the first hydrophilic material block, three hydrophilic material monomers (m=3) are connected, for second hydrophilic material blocks, five hydrophilic material monomers (m=5) are connected, and for the third hydrophilic material block, four hydrophilic material monomers (m=4) are connected. Alternatively, the same number of hydrophilic material monomers may be used for all hydrophilic material blocks.

According to the present invention, the linker (J) is preferably selected from the group consisting of $PO_3^-$, $SO_3$ and $CO_2$, but is not limited thereto. Depending on the monomer of the used hydrophilic material or the like, any linker may be used so long as it satisfies the object of the present invention and is obvious to those skilled in the art.

The entirety or part of the hydrophilic material monomer may be modified to have a functional group required for bonding to other substances such as a target specific ligand.

In some cases, one to three phosphate groups may be bonded to the 5' end of the antisense strand of a double-stranded oligo RNA structure comprising specific miRNA for the gene.

For example, the double-stranded oligo RNA structure comprising miRNA has a structure represented by the following Formula (3") or Formula (4"):

$(A_m-J)_n$-X-5'S3'-Y-B

3'AS5'-$PO_4$                          [Formula (3")]

$(J-A_m)_n$-X-5'S3'-Y-B

3'AS5'-$PO_4$                          [Formula (4")]

The hydrophobic material (B) functions to form nanoparticles having an oligonucleotide structure represented by Formula (1) through hydrophobic interaction.

The hydrophobic material preferably has a molecular weight of 250 to 1,000, and may be a steroid derivative, a glyceride derivative, glycerol ether, polypropylene glycol, $C_{12}$ to $C_{50}$ unsaturated or saturated hydrocarbon, diacylphosphatidylcholine, fatty acid, phospholipid, lipopolyamine or the like, but is not limited thereto. Any hydrophobic material may be used without limitation so long as it satisfies the objects of the present invention, which is obvious to those skilled in the art to which the present invention pertains.

The steroid derivative may be selected from the group consisting of cholesterol, cholestanol, cholic acid, cholesteryl formate, cholestanyl formate and cholestanylamine, and the glyceride derivative may be selected from mono-, di- and tri-glyceride and the like, wherein the fatty acid of glyceride is preferably a $C_{12}$ to $C_{50}$ unsaturated or saturated fatty acid.

In particular, among the hydrophobic materials, saturated or unsaturated hydrocarbon or cholesterol is preferred for easy binding to oligonucleotide during synthesis of the oligonucleotide structures according to the present invention.

The hydrophobic material is bonded to the distal end of the hydrophilic material and may be bonded to the sense strand or antisense strand of miRNAs.

According to the present invention, the hydrophilic material, the hydrophilic material block or the hydrophobic material is bonded to oligonucleotide through a simple covalent bond or linker-mediated covalent bond (X or Y). The covalent bond may be a non-degradable or degradable bond. Examples of the non-degradable bond include an amide bond or a phosphoryl bond, and the degradable bond includes a disulfide bond, an acid-degradable bond, an ester bond, an anhydride bond, a biodegradable bond, an enzyme-degradable bond or the like, but is not limited thereto.

Figure 9A:
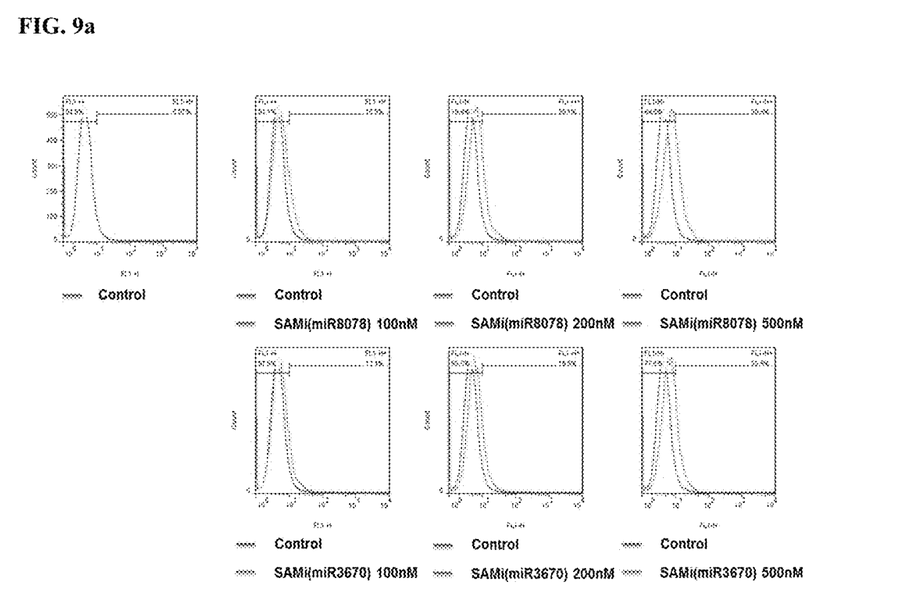
FIGS. 9A and 9B are images showing comparison in induction of apoptosis mechanisms, when treating lung cancer cell lines with an oligo RNA structure containing a miRNA sequence, and then staining with Annexin V.
Figure 9B:
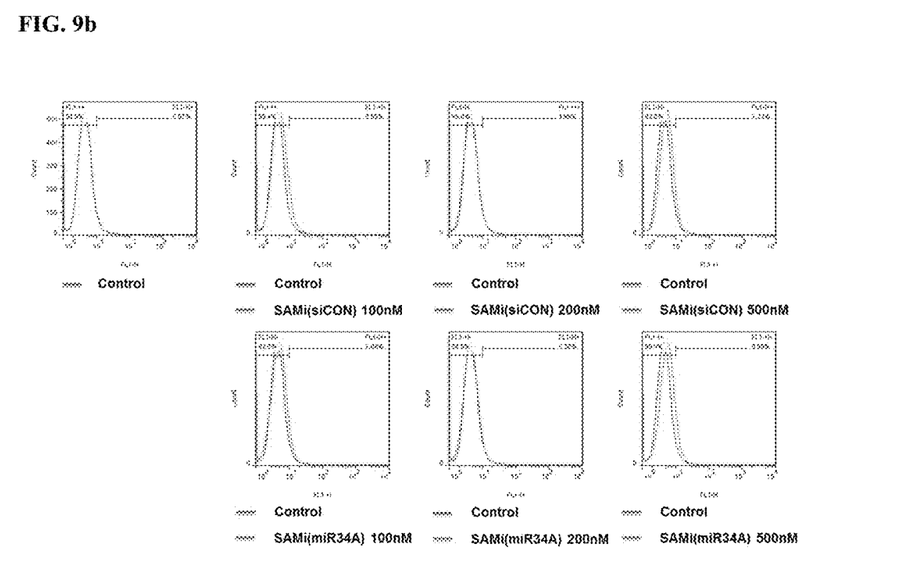

The miRNA oligo structures according to the present invention were produced and in vitro treated with lung cancer cell lines, and the cell lines were stained with Annexin V and were analyzed by flow cytometry. As can be seen from FIGS. 9A and 9B, when nanoparticles were used to improve in vivo stability using the RNA structure, apoptosis of cell lines can be concentration-dependently induced.

Based on this, the present invention relates to a composition for preventing or treating cancer comprising the oligonucleotide structure. The present invention also relates to a method for preventing or treating cancer comprising a step of administering the oligonucleotide structure.

According to the present invention, the cancer is at least one selected from the group consisting of primary cancer such as lung cancer, liver cancer, stomach cancer, colon cancer, pancreatic cancer, gall bladder cancer, biliary tract cancer, breast cancer, leukemia, esophageal cancer, non-Hodgkin's lymphoma, thyroid cancer, cervical cancer and skin cancer, and metastatic cancer caused by metastasis from primary cancer to other organs, and tumor-associated cell diseases caused by promotion of abnormal excessive cell division, but the present invention is not limited thereto.

The miRNA sequence that can be used as an active ingredient of the composition for treating cancer provided by the present invention is a sequence derived from the human genome, however, a miRNA sequence obtained from the genome derived from another animal also can be used without limiting the genome of the miRNA The miRNA can be used in the form of various miRNA derivatives (miRNA mimics) that generate the bioequivalence efficacy of miRNAs, and can be modified miRNAs containing miRNA sequences containing the same seed region. At this time, the length of sequence 1 or sequence 2 can be reduced, and a short derivative consisting of 15 nucleotides can also be used.

The miRNA derivatives for miRNAs may partially include a phosphorothiolate structure in which O in the RNA phosphate backbone structure is replaced with another element such as sulfur, and can be used in the forms wherein DNA, PNA (peptide nucleic acid) and LNA (locked nucleic acid) molecules are entirely or partially replaced with RNA and can be used in the forms wherein the 2' hydroxyl group of RNA sugar is replaced with various functional structures, and examples of such modifications include, but are not limited to, methylation, methoxylation, fluorination and the like.

The miRNA is not limited to mature miRNA and the double stranded RNA of the miRNA derivative derived therefrom, and can be used in the form of a miRNA precursor and, for the miRNA precursor, aforementioned partial or entire replacement of the RNA phosphate backbone structure and RNA nucleic acid with DNA, PNA, LNA and the like, and modification of the 2' hydroxyl group of the RNA sugar molecule are possible.

The miRNA can be used in the form of precursor miRNA or primary miRNA (pri-miRNA) and can be synthesized by a chemical method or delivered in the form of a plasmid to cells which express the same.

According to the present invention, methods for delivering miRNAs to cells cultured on culture dishes include, but are not limited to, mixing with cationic lipids, using electrical stimulation, and using viruses.

The composition for treating cancer comprising the miRNA as an active ingredient may be a pharmaceutical composition further containing a pharmaceutically acceptable carrier and may be formulated together with a carrier.

The term "pharmaceutically acceptable carrier" as used herein refers to a carrier or diluent that does not impair biological activities or properties of an administered compound without stimulating an organism. Acceptable pharmaceutical carriers for compositions, which are formulated into liquid solutions, are sterilized and biocompatible and examples thereof include saline, sterile water, Ringer's solution, buffered saline, albumin injection solutions, dextrose solutions, maltodextrin solutions, glycerol, ethanol and mixtures thereof. If necessary, other conventional additives such as antioxidants, buffers and bacteriostatic agents may be added. In addition, diluents, dispersants, surfactants, binders and lubricants can be additionally added to formulate injectable solutions such as aqueous solutions, suspensions and emulsions, pills, capsules, granules or tablets.

The composition for preventing or treating cancer comprising the miRNA and the pharmaceutically acceptable carrier can be applied to any formulation containing the same as an active ingredient and can be prepared for oral or parenteral formulation. The pharmaceutical formulation may include formulations suitable for oral, rectal, nasal, topical (including under the cheek and tongue), subcutaneous, vaginal or parenteral (including intramuscular, subcutaneous and intravenous) administration, or inhalation or insufflation. Examples of formulations for oral administration containing the composition of the present invention as an active ingredient include tablets, troches, lozenges, aqueous or oily suspensions, prepared powders or granules, emulsions, hard or soft capsules, syrups or elixirs. In order to prepare formulations such as tablets and capsules, a binder such as lactose, saccharose, sorbitol, mannitol, starch, amylopectin, cellulose or gelatin, an excipient such as dicalcium phosphate, a disintegrating agent such as corn starch or sweet potato starch, a lubricant such as calcium stearate, sodium stearyl fumarate or polyethyleneglycol wax can be incorporated, and capsule formulations may further contain a liquid carrier such as a fatty oil, in addition to the above-mentioned ingredients.

Examples of the formulations for parenteral administration containing the composition of the present invention as an active ingredient include injection forms such as subcutaneous injection, intravenous injection or intramuscular injection, suppository or spray forms such as aerosols inhalable through a breathing apparatus. For preparation into injectable formulations, the compositions of the present invention can be mixed in water with stabilizers or buffers to prepare solutions or suspensions and the solutions or suspensions can be formulated on the basis of an ampule or vial unit for administration. For suppository injection, compositions for rectal administration such as suppositories containing a conventional suppository base such as cocoa butter or other glycerides or enema preparations can be formulated. For spray formulation such as an aerosol, an additive such as a propellant may be mixed such that a water-dispersed concentrate or wet powder is dispersed.

Hereinafter, the present invention will be described in more detail with reference to examples. However, it is obvious to those skilled in the art that these examples are provided only for illustration of the present invention and should not be construed as limiting the scope of the present invention.

EXAMPLE 1 PRODUCTION OF miRNA SCREENING LIBRARY

As 21-version human miRNA sequences provided from the miRNA database, miRBase (www.mirbase.org), double-stranded sequences of miRNA were synthesized by a solid synthesis method used for common synthesis of oligo from 1,700 miRNA screening libraries, based on the stem-loop structure. Each strand of the synthesized miRNA was purified by reverse phase separation using a C18 resin. Whether or not the intended sequence was synthesized for all synthesized miRNA strands was detected and identified with a MALDI-TOF mass spectrometer. In order to prepare double-stranded miRNAs, the synthesized miRNA strands and the corresponding complementary strands were heated in the presence of a salt at 95° C. for 2 minutes and then slowly cooled. Sequences 1 of respective tested double-stranded miRNAs are represented by SEQ ID NO. 70 to SEQ ID NO. 1797 in this order and Sequences 2 thereof are represented by SEQ ID NO. 1798 to 3525 in this order.

EXAMPLE 2 MEASUREMENT OF ACTIVITY OF miRNA LIBRARY SAMPLES

Figure 1:
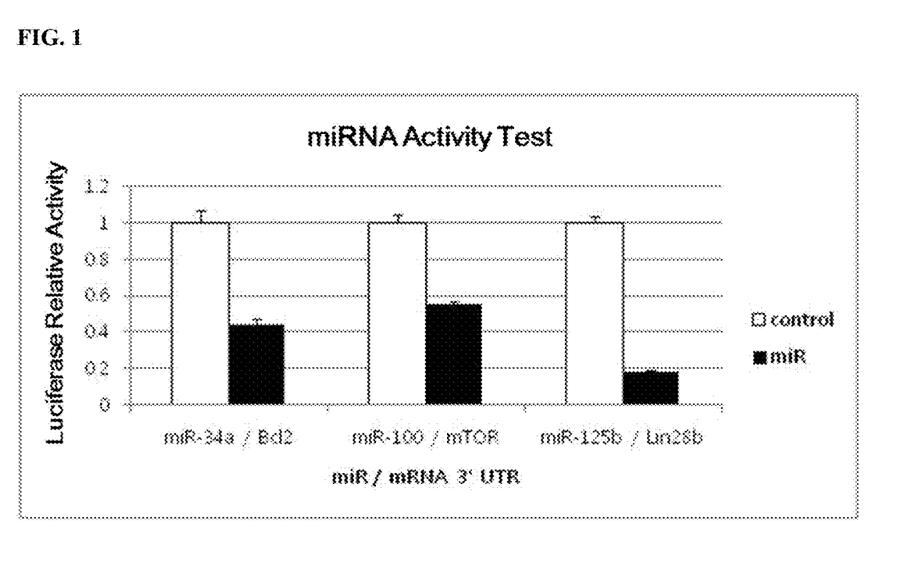
FIG. 1 is a graph showing test results regarding inhibitory activities against protein expression by miR-34a, miR-100 and miR-125b, which are representatively selected from the entire screening library, and each mRNA 3' UTR whose expression is known to be inhibited by miR-34a, miR-100 and miR-125b is inserted into the 3' UTR of the luciferase expression vector, in order to identify the activity of the miRNAs.

In order to identify whether or not miRNA double strands synthesized in Example 1 were active, miR-34a, miR-100 and miR-125b were selectively selected from about 1,700 types of miRNA screening libraries. miRNAs have been selected based on the large number of studies previously performed on the types of target mRNAs that control functions and expression and the binding sites that bind to each mRNA 3' UTR. The 3' UTR sites of Bcl2, mTOR and Lin28b mRNAs, which are known to be regulated by miR-34a, miR-100 and miR-125b, respectively, are replaced with the 3' UTR sites of the firefly luciferase vector to produce vectors corresponding to respective miRNAs. The HEK-293T cell lines were co-transfected with each vector and miR control group, or miR-34a, miR-100 and miR-125b corresponding to each vector, using an intracellular delivery reagent of oligo, Lipofectamine 2000 (Invitrogen) (three replicate samples) and cultured at 37° C. and 5% (v/v) carbon dioxide for 24 hours. The activity of luciferase was measured using a luminometer (Thermo Scientific) to identify the activity of the synthesized miRNA (FIG. 1).

Figure 2:
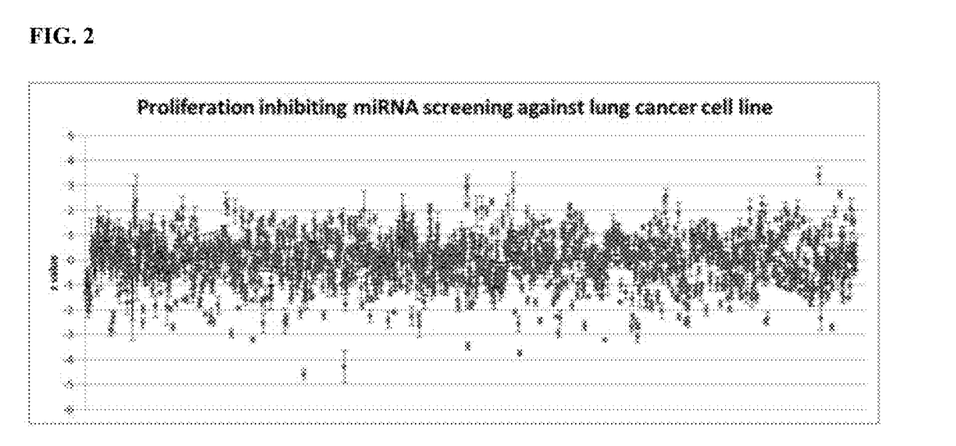
FIG. 2 is a graph showing results, when treating NCI-H460 lung cancer cell lines with a screening library composed of 1,700 kinds of miRNAs, quantifying cell growth using Resazurin reagent and then converting the resulting value into a relative growth value.

EXAMPLE 3 SCREENING FOR IDENTIFYING MICRO RNAs INDUCING INHIBITION OF PROLIFERATION OF LUNG CANCER CELL LINES 3,000 to 10,000 NCI-H460 cells were seeded on a 96-well plate and cultured at 37° C., and 5% (v/v) carbon dioxide for 24 hours. Each miRNA of the miRNA library was transfected using RNAiMAX reagent (Invitrogen) to a final concentration of 100 nM. Each miRNA was transfected three times, which means that three 96-well plates for each miRNA library stored on a 96-well plate were prepared. The cells were further cultured for 24 hours under the same conditions as the cell culture conditions described above, and the fluorescence value generated by adding Resazurin reagent (Promega) was measured using a fluorescence meter (Fluoremeter, Tecan). In order to comparatively evaluate the ability of each miRNA to inhibit cell proliferation, a mean value and a standard deviation of 96 values measured on the 96-well plate were determined. The difference according to standard deviation multiple between the measured value in each miRNA-containing well and the mean value was calculated in accordance with the following (Z-score) formula:

$$z_i = \frac{x_i - \mu}{\sigma}$$

wherein $x_i$ is the measured value of each well, $\mu$ is the mean value of the whole well of the plate, and $\sigma$ is the standard deviation. The standard deviation multiple, $z_i$, of each well was the mean value obtained from the three plate replicates, and was used to select 50 primary candidate miRNAs having a z value less than −2 (FIG. 2, Table 2).

TABLE 2

Primarily-screened miRNA sequences

| | | |
|---|---|---|
| SEQ ID NO. 1 hsa-miR-23c | strand 1 | AUCACAUUGCCAGUGAUUACCC |
| SEQ ID NO. 2 hsa-miR-23c | strand 2 | GUAAUCACUGGCAAUGUGAUUU |
| SEQ ID NO. 3 hsa-miR-219b | strand 1 | AGAUGUCCAGCCACAAUUCUCG |
| SEQ ID NO. 4 hsa-miR-219b | strand 2 | AGAAUUGCGUUUGGACAAUCAGU |
| SEQ ID NO. 5 hsa-miR-378c | strand 1 | ACUGGACUUGGAGUCAGAAGAGUGG |
| SEQ ID NO. 6 hsa-miR-378c | strand 2 | ACUCUUCUGACUCCAAGUCCAGUUU |
| SEQ ID NO. 7 hsa-miR-548aa | strand 1 | AAAAACCACAAUUACUUUUGCACCA |
| SEQ ID NO. 8 hsa-miR-548aa | strand 2 | GUGCAAAAGUAAUUGUGGUUUUUUU |
| SEQ ID NO. 9 hsa-miR-548u | strand 1 | CAAAGACUGCAAUUACUUUUGCG |
| SEQ ID NO. 10 hsa-miR-548u | strand 2 | CAAAAGUAAUUGCAGUCUUUGUU |
| SEQ ID NO. 11 hsa-miR-571 | strand 1 | UGAGUUGGCCAUCUGAGUGAG |
| SEQ ID NO. 12 hsa-miR-571 | strand 2 | CACUCAGAUGGCCAACUCAUU |
| SEQ ID NO. 13 hsa-miR-641 | strand 1 | AAAGACAUAGGAUAGAGUCACCUC |
| SEQ ID NO. 14 hsa-miR-641 | strand 2 | GGUGACUCUAUCCUAUGUCUUUUU |
| SEQ ID NO. 15 hsa-miR-1244 | strand 1 | AAGUAGUUGGUUUGUAUGAGAUGGUU |
| SEQ ID NO. 16 hsa-miR-1244 | strand 2 | CCAUCUCAUACAAACCAACUACUUUU |
| SEQ ID NO. 17 hsa-miR-1248 | strand 1 | ACCUUCUUGUAUAAGCACUGUGCUAAA |
| SEQ ID NO. 18 hsa-miR-1248 | strand 2 | UAGCACAGUGCUUAUACAAGAAGGUUU |
| SEQ ID NO. 19 hsa-miR-1298 | strand 1 | CAUCUGGGCAACUGACUGAAC |
| SEQ ID NO. 20 hsa-miR-1298 | strand 2 | UUCAUUCGGCUGUCCAGAUGUA |
| SEQ ID NO. 21 hsa-miR-2392 | strand 1 | UAGGAUGGGGGUGAGAGGUG |
| SEQ ID NO. 22 hsa-miR-2392 | strand 2 | CCUCUCACCCCCAUCCUAUU |

TABLE 2-continued

Primarily-screened miRNA sequences

| SEQ ID NO. 23 | hsa-miR-3119 | strand 1 | UGGCUUUUAACUUUGAUGGC |
| SEQ ID NO. 24 | hsa-miR-3119 | strand 2 | CAUCAAAGUUAAAAGCCAUU |
| SEQ ID NO. 25 | hsa-miR-3164 | strand 1 | UGUGACUUUAAGGGAAAUGGCG |
| SEQ ID NO. 26 | hsa-miR-3164 | strand 2 | CCAUUUCCCUUAAAGUCACAUU |
| SEQ ID NO. 27 | hsa-miR-3188 | strand 1 | AGAGGCUUUGUGCGGAUACGGGG |
| SEQ ID NO. 28 | hsa-miR-3188 | strand 2 | CCGUAUCCGCACAAAGCCUCUUU |
| SEQ ID NO. 29 | hsa-miR-3609 | strand 1 | CAAAGUGAUGAGUAAUACUGGCUG |
| SEQ ID NO. 30 | hsa-miR-3609 | strand 2 | GCCAGUAUUACUCAUCACUUUGUU |
| SEQ ID NO. 31 | hsa-miR-3612 | strand 1 | AGGAGGCAUCUUGAGAAAUGGA |
| SEQ ID NO. 32 | hsa-miR-3612 | strand 2 | CAUUUCUCAAGAUGCCUCCUUU |
| SEQ ID NO. 33 | hsa-miR-3662 | strand 1 | GAAAAUGAUGAGUAGUGACUGAUG |
| SEQ ID NO. 34 | hsa-miR-3662 | strand 2 | UCAGUCACUACUCAUCAUUUUCUU |
| SEQ ID NO. 35 | hsa-miR-3670 | strand 1 | AGAGCUCACAGCUGUCCUUCUCUA |
| SEQ ID NO. 36 | hsa-miR-3670 | strand 2 | GAGAAGGACAGCUGUGAGCUCUUU |
| SEQ ID NO. 37 | hsa-miR-3943 | strand 1 | UAGCCCCCAGGCUUCACUUGGCG |
| SEQ ID NO. 38 | hsa-miR-3943 | strand 2 | CCAAGUGAAGCCUGGGGGCUAUU |
| SEQ ID NO. 39 | hsa-miR-4424 | strand 1 | AGAGUUAACUCAAAAUGGACUA |
| SEQ ID NO. 40 | hsa-miR-4424 | strand 2 | GUCCAUUUUGAGUUAACUCUUU |
| SEQ ID NO. 41 | hsa-miR-4461 | strand 1 | GAUUGAGACUAGUAGGGCUAGGC |
| SEQ ID NO. 42 | hsa-miR-4461 | strand 2 | CUAGCCCUACUAGUCUCAAUCUU |
| SEQ ID NO. 43 | hsa-miR-4477a | strand 1 | CUAUUAAGGACAUUUGUGAUUC |
| SEQ ID NO. 44 | hsa-miR-4477a | strand 2 | AUCACAAAUGUCCUUAAUAGUU |
| SEQ ID NO. 45 | hsa-miR-4477b | strand 1 | AUUAAGGACAUUUGUGAUUGAU |
| SEQ ID NO. 46 | hsa-miR-4477b | strand 2 | CAAUCACAAAUGUCCUUAAUUUU |
| SEQ ID NO. 47 | hsa-miR-4765 | strand 1 | UGAGUGAUUGAUAGCUAUGUUC |
| SEQ ID NO. 48 | hsa-miR-4765 | strand 2 | ACAUAGCUAUCAAUCACUCAUU |
| SEQ ID NO. 49 | hsa-miR-4773 | strand 1 | CAGAACAGGAGCAUAGAAAGGC |
| SEQ ID NO. 50 | hsa-miR-4773 | strand 2 | CUUUCUAUGCUCCUGUUCUGUU |
| SEQ ID NO. 51 | hsa-miR-4776 | strand 1 | GUGGACCAGGAUGGCAAGGGCU |
| SEQ ID NO. 52 | hsa-miR-4776 | strand 2 | CUUGCCAUCCUGGUCCACUGCAU |
| SEQ ID NO. 53 | hsa-miR-4999 | strand 1 | UGCUGUAUUGUCAGGUAGUGA |
| SEQ ID NO. 54 | hsa-miR-4999 | strand 2 | UCACUACCUGACAAUACAGU |
| SEQ ID NO. 55 | hsa-miR-5096 | strand 1 | GUUUCACCAUGUUGGUCAGGC |
| SEQ ID NO. 56 | hsa-miR-5096 | strand 2 | CUGACCAACAUGGUGAAACUU |
| SEQ ID NO. 57 | hsa-miR-5697 | strand 1 | UCAAGUAGUUUCAUGAUAAAGG |
| SEQ ID NO. 58 | hsa-miR-5697 | strand 2 | UUUAUCAUGAAACUACUUGAUU |
| SEQ ID NO. 59 | hsa-miR-5705 | strand 1 | UGUUUCGGGGCUCAUGGCCUGUG |
| SEQ ID NO. 60 | hsa-miR-5705 | strand 2 | CAGGCCAUGAGCCCCGAAACAUU |
| SEQ ID NO. 61 | hsa-miR-5707 | strand 1 | ACGUUUGAAUGCUGUACAAGGC |

TABLE 2-continued

Primarily-screened miRNA sequences

| | | | |
|---|---|---|---|
| SEQ ID NO. 62 | hsa-miR-5707 | strand 2 | CUUGUACAGCAUUCAAACGUUU |
| SEQ ID NO. 63 | hsa-miR-8053 | strand 1 | UGGCGAUUUUGGAACUCAAUGGCA |
| SEQ ID NO. 64 | hsa-miR-8053 | strand 2 | CCAUUGAGUUCCAAAAUCGCCAUU |
| SEQ ID NO. 65 | hsa-miR-8078 | strand 1 | GGUCUAGGCCCGGUGAGAGACUC |
| SEQ ID NO. 66 | hsa-miR-8078 | strand 2 | GUCUCUCACCGGGCCUAGACCUU |

EXAMPLE 4 SECONDARY SCREENING FOR IDENTIFYING MICRO RNAs WITH INHIBITORY ACTIVITY AGAINST PROLIFERATION OF LUNG CANCER CELL LINES

Figure 3:
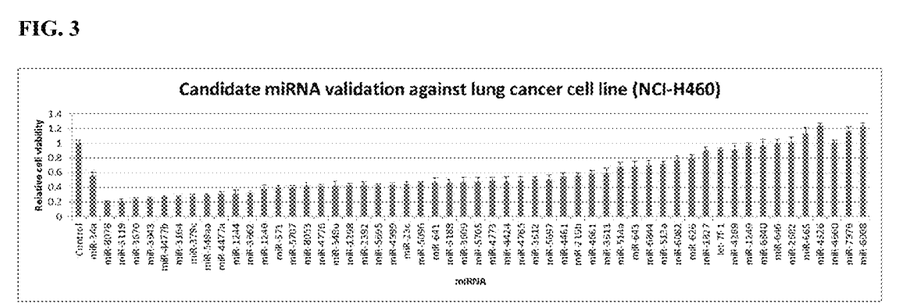
FIG. 3 is a graph showing results when selecting about 50 kinds of miRNAs showing excellent efficacy in NCI-H460 cell lines and measuring relative inhibitory activity against cancer cell growth with WST-1 reagent using the miRNAs.

Secondary screening was carried out by improving the measurement accuracy using 50 miRNA candidates group obtained by primary screening. The test conditions were the same as the primary screening conditions, except that WST-1 reagent (Roche) was used as a reagent for measuring cell proliferation ability, instead of resazurin. WST-1 was used because of the advantage of the capability of measuring the intensity of signal more quantitatively than resazurin. Measured values of cell inhibitory ability by each miRNA are shown relative to the control in FIG. 3, and miR-34a was also included as a positive control.

EXAMPLE 5 ANALYSIS OF CAPABILITY TO INDUCE CELL APOPTOSIS

Figure 4:
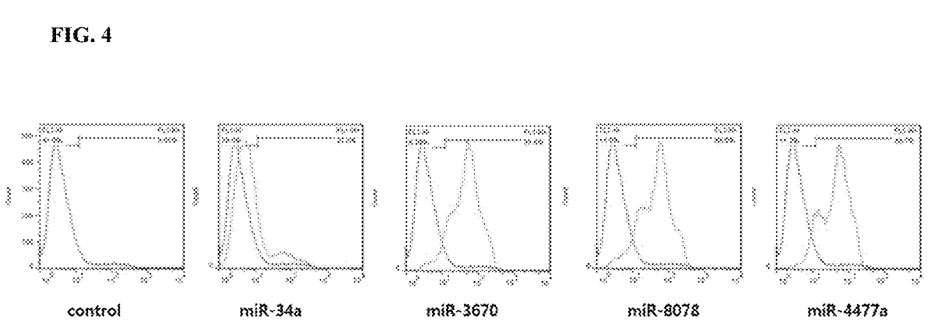
FIG. 4 shows results, when injecting miR-34a, miR-3670, miR-8078 and miR-4477a by transfection into cells in order to measure apoptotic effects in lung cancer cell lines, staining Annexin V labeled with FITC dye and then analyzing the degree of cell death with a flow cytometer.

The method used for screening is to measure the degree of relative inhibition of cell proliferation by measuring the number of cells in a quantitative sense. The mechanisms that inhibit cell proliferation include a method of reducing the cell cycle rate and a method of inducing apoptosis. In order to analyze the mechanisms of inhibitory activity of miRNAs found in the present invention against cell proliferation, the degree of apoptosis was analyzed by flow cytometry (fluorescence activated cell sorter (FACS)). For this purpose, cells were seeded on a 6-well plate, and the miRNA was injected into the cells using RNAiMAX reagent. Then, cells were cultured under the conditions described above for 48 hours. Then, the cells were treated with annexin V labeled with FIT-C fluorescent dye and analyzed by flow cytometry (FIG. 4). Analysis results showed that most of the cells treated with miR-3670, miR-4477a and miR-8078 were killed. This indicates that inhibition of tumor growth of the miRNA identified in the screening is caused by inducing apoptosis (Table 3).

TABLE 3

Finally-screened miRNA sequences

| | | | |
|---|---|---|---|
| SEQ ID NO. 35 | hsa-miR-3670 | strand 1 | AGAGCUCACAGCUGUCCUUCUCUA |
| SEQ ID NO. 36 | hsa-miR-3670 | strand 2 | GAGAAGGACAGCUGUGAGCUCUUU |
| SEQ ID NO. 67 | miR-IC | IC | GACUGGUAUAGCUGCUUUUGGAGCCUCA |
| SEQ ID NO. 43 | hsa-miR-4477a | strand 1 | CUAUUAAGGACAUUUGUGAUUC |
| SEQ ID NO. 44 | hsa-miR-4477a | strand 2 | AUCACAAAUGUCCUUAAUAGUU |
| SEQ ID NO. 68 | miR-4477a-IC | IC | AUCACAAAUGUCCUUAAUGGCA |
| SEQ ID NO. 65 | hsa-miR-8078 | strand 1 | GGUCUAGGCCCGGUGAGAGACUC |
| SEQ ID NO. 66 | hsa-miR-8078 | strand 2 | GUCUCUCACCGGGCCUAGACCUU |
| SEQ ID NO. 69 | miR-IC | IC | CUCCACCGGGCUGACCGGCCUG |

EXAMPLE 6 INHIBITION OF TUMOR GROWTH IN SOFT AGAR BY miRNA

Figure 5:
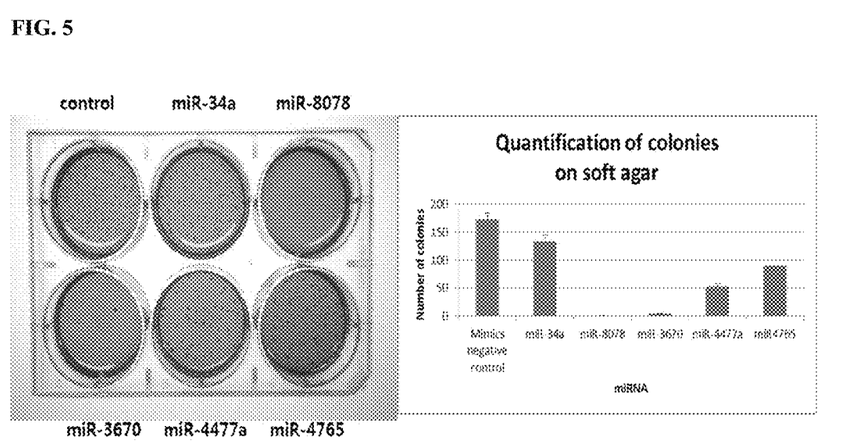
FIG. 5 shows measurement results regarding effects of miRNAs on clustering ability of lung cancer cell lines, after injecting each miRNA by transfection into lung cancer cell lines and culturing in soft agar for 2 weeks.

By culturing tumor cells using soft agar, the characteristics of the tumor cells can be measured. Normal cells require a support such as a culture dish to grow, whereas tumor cells tend to grow under an environment free from a physically rigid support such as soft agar. Cell clustering ability in soft agar was determined using these tumor specific properties. NCI-H460 lung cancer cell lines were treated with control miRNA, miR-34a, miR-8078, miR-3670, miR-4477a and miR-4765, cultured for 24 hours, mixed with soft agar, and cultured on a 6 well-plate for 2 weeks. The cells were stained with a crystal violet dye and the numbers of clusters were counted (FIG. 5). Results showed that the cells treated with miR-8078 and miR-3670 formed almost no clusters, and that the cells treated with miR-4477a showed about 30% of cluster formation ability as compared with the control.

EXAMPLE 7 MEASUREMENT OF INHIBITORY ACTIVITY OF miRNAs TARGET mRNAs AGAINST CELL PROLIFERATION

Target mRNAs, whose protein expression is controlled by miRNA, have a sequence partially complementary to the sequence of the miRNAs. In order to inhibit expression of mRNAs, the sequence of the seed region for miRNAs is particularly important, because it binds to mRNA having a sequence complementary to the seed region sequence to inhibit gene expression. However, because the seed region sequence is relatively short, i.e., 8 to 9 bases, the mRNA targeted by the miRNA is estimated using software. However, even when software is used, it is known that only some of the estimated targets are actual targets. In order to solve this difficulty, the target genes predicted through software were treated with siRNA to reduce intracellular content and were selected by determining whether or not cell growth was inhibited. TargetScan was used as a target prediction software generally used in the art in order to predict the target mRNA of miRNA, and the total 600 types of genes were selected as estimated targets of miR-3670, miR-4477a and miR-8078. Three siRNAs were synthesized for each gene selected, and the same experiment was conducted as in Example 3 using the siRNAs. Cells were seeded on 96-well plates, treated with each siRNA and cultured for 48 hours, and then cell proliferation was measured using a resazurin reagent. The Z-score of each gene was calculated from the mean of the measurement values of a total of about 1,800 (600 genes×3 kinds of siRNAs) in the same manner as in Example 3 and shown in FIG. 6.

EXAMPLE 8 ANALYSIS OF TARGET mRNA OF miRNA

The action mode of miRNAs deteriorates production of proteins from mRNAs and, at the same time, causes the degradation of most of the target mRNAs. Accordingly, miRNAs are injected into cells and the contents of mRNAs, which are the targets of miRNAs, are analyzed using qPCR, and the decrease in the content is measured, which can be used as a criterion for determining the target mRNA of miRNAs. In order to determine whether the target mRNAs were substantially degraded, when the miRNAs were transferred into cells, while targeting the target genes of miRNAs identified in Example 7, miR-3677, miR-4477a and miR-8078 were transfected into lung cancer cell line and then cultured for 48 hours, and RNAs were extracted from respective cells to quantitatively measure RNA contents (FIG. 7). Results showed that the predicted target mRNA contents of miR-3670, miR-4477a and miR-8078 were remarkably lowered.

EXAMPLE 9 IDENTIFICATION OF TARGET mRNAs BY LUCIFERASE ASSAY

Because miRNAs inhibit production of proteins from target mRNAs by binding to the 3' UTR (untranslated region) of target mRNAs, luciferase assay is commonly used as a method for directly measuring the relationships between miRNAs and target mRNAs. The TargetScan software provides the 3' UTR sequence containing the miRNA-binding sequence. The 3' UTR sequence was inserted by gene cloning into the 3' UTR of firefly luciferase as described in Example 2, and the vector produced in this manner was transfected into human embryonic kidney (HEK) cells simultaneously with the corresponding miRNA to measure the expression level of luciferase in the vector. At this time, renilla luciferase was also transfected simultaneously to calibrate the transfection efficiency. miRNA, firefly luciferase and Renilla luciferase were simultaneously injected and cultured for 48 hours and then measured with a luminometer (FIG. 8). Results showed that each target mRNA is directly controlled by the corresponding miRNA.

EXAMPLE 10 SYNTHESIS OF RNA OLIGO STRUCTURE

The double-stranded oligo RNA structure produced according to the present invention has a structure represented by the following Formula (5):

$$3'AS5'\text{-}PO_4 \qquad \text{[Formula (5)]}$$

wherein S represents a sense strand of miRNA, AS represents an anti-sense strand of miRNA, $PO_4$ represents a phosphate group, ethylene glycol is a hydrophilic material monomer, and hexaethylene glycols are bonded to through a phosphate group ($PO_3$-) as a linker (J), $C_{24}$ represents a tetradocosane containing a disulfide bond as a hydrophobic material, and 5' and 3' represent the end directions of double-stranded oligo RNA.

Regarding the sense strand of miRNA in Formula (5), a phosphodiester bond constituting an RNA backbone structure using β-cyanoethyl phosphoamidite and DMT-hexaethyl glycol-CPG as a support is linked, so an oligo RNA-hydrophilic material structure containing the sense strand wherein hexaethylene glycol is bonded to the 3' end is synthesized, and then tetradodecanoic acid containing a disulfide bond is bonded at the 5' end, to form a desired RNA-polymer structure of the sense strand. In the case of the antisense strand to be annealed with the strand, an antisense strand of the sequence complementary to the sense strand was prepared through the aforementioned reaction.

EXAMPLE 11 INDUCTION OF CELL APOPTOSIS MECHANISMS BY RNA STRUCTURE CONTAINING miRNA SEQUENCE

The RNA oligo structure was prepared by the method in accordance with Example 10 in order to ensure in vivo stability of the miRNA selected through Examples described above. In order to evaluate whether or not nanoparticles produced in this manner induced apoptosis in lung cancer cell lines, the lung cancer cell lines were seeded and cultured on a 6-well plate. The nanoparticles with different concentrations for respective wells were added to a culture medium. 48 hours after addition of the nanoparticles, the cells were stained with Annexin V labeled with an FIT-C fluorescent dye, and the degree of apoptosis was analyzed by flow cytometry. As can be seen from FIGS. 9A and 9B, miRNAs as the RNA structure kill cells dependent upon the concentration of treated miRNAs.

INDUSTRIAL APPLICABILITY

The double-stranded oligo RNA structure and the composition for treating cancer containing the same according to the present invention include at least one miRNA selected from the group consisting of miR-3670, miR-4477a and miR-8078, thereby being widely used as an anti-cancer therapeutic agent because of improved anti-cancer effects, as compared to the pharmaceutical composition for treating cancer containing miR-34a and other miRNAs as an active ingredient.

Although specific configurations of the present invention has been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11123361B2). An electronic copy of the "Sequence Listing" will also be available from the USPTO upon request and payment of the fee set forth in 37 CFR 1.19(b)(3).

The invention claimed is:

1. A method for treating a lung cancer, comprising administering to a subject in need thereof a double-stranded oligo RNA structure comprising the following Formula (1):

A-X-R-Y-B            Formula (1)

wherein A represents a hydrophilic material, B represents a hydrophobic material, X and Y each independently represent a simple covalent bond or a linker-mediated covalent bond, and R represents an at least one miRNA, wherein said miRNA is miR-3670.

2. The method of claim 1, wherein the miRNA treats cancer by inducing apoptosis of cancer cell.

3. The method of claim 1, wherein the hydrophilic material is represented by $(A)_n$, $(A_m-J)_n$ or $(J-A_m)_n$, wherein A represents a hydrophilic material monomer, n represents 1 to 200, m represents 1 to 15, and J represents a linker that links m hydrophilic material monomers to one another, or links m hydrophilic material monomers to oligonucleotides.

4. The method of claim 1, wherein the hydrophilic material has a molecular weight of 200 to 10,000.

5. The method of claim 1, wherein the hydrophilic material is polyethylene glycol (PEG).

6. The method of claim 3, wherein the hydrophilic material monomer is the following compound (1):

Compound (1)

wherein Gin Compound (1) is selected from the group consisting of $CH_2$, O, S, and NH.

7. The method of claim 3, wherein the linker (J) is selected from the group consisting of $PO_3^-$, $SO_3$, and $CO_2$.

8. The method of claim 1, wherein the hydrophobic material has a molecular weight of 250 to 1,000.

9. The method of claim 1, wherein the hydrophobic material is selected from the group consisting of a steroid derivative, a glyceride derivative, glycerol ether, polypropylene glycol, $C_{12}$ to $C_{50}$ unsaturated or saturated hydrocarbon, diacyl-phosphatidylcholine, fatty acid, phospholipid, and lipopolyamine.

10. The method of claim 9, wherein the steroid derivative is selected from the group consisting of cholesterol, cholestanol, cholic acid, cholesteryl formate, cholestanyl formate and cholestanylamine.

11. The method of claim 9, wherein the glyceride derivative is selected from mono-, di- and tri-glyceride.

12. The method of claim 1, wherein the covalent bond represented by X and Y is a non-degradable or degradable bond.

13. The method of claim 12, wherein the non-degradable bond is an amide bond or a phosphoryl bond.

14. The method of claim 12, wherein the degradable bond is a disulfide bond, an acid-degradable bond, an ester bond, an anhydride bond, a biodegradable bond or an enzyme-degradable bond.

15. The method of claim 1, wherein miR-3670 comprises a double stranded RNA comprising a base sequence of SEQ ID NO. 35; and a base sequence of SEQ ID NO. 36 or SEQ ID NO. 67.

* * * * *

UNITED STATES PATENT AND TRADEMARK OFFICE
CERTIFICATE OF CORRECTION

| | | |
|---|---|---|
| PATENT NO. | : 11,123,361 B2 | Page 1 of 1 |
| APPLICATION NO. | : 16/302670 | |
| DATED | : September 21, 2021 | |
| INVENTOR(S) | : Lee et al. | |

It is certified that error appears in the above-identified patent and that said Letters Patent is hereby corrected as shown below:

On the Title Page

Item (54), in Line 2 of title, "MIRNA" should be -- miRNA --.

In the Specification

Column 1, Line 2, "MIRNA" should be -- miRNA --.

Column 8, Line 39, "2584-(2013))." should be -- 2584-91 (2013)). --.

Column 10, Line 40, "39269-(2011);" should be -- 39269-81 (2011); --.

Column 11, Line 3, "CKAPS" should be -- CKAP5 --.

Column 12, Lines 17-18, "n represents 1 to 200, represents 1 to 15" should be -- n represents 1 to 200, m represents 1 to 15 --.

Column 12, Line 55, "Gin" should be -- G in --.

Column 13, Line 1, "TABLE 2" should be -- TABLE 1 --.

In the Claims

Column 26, Line 14, "Gin" should be -- G in --.

Column 25, Line 22, "represents an at least one miRNA" should be -- represents an miRNA --.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*